United States Patent [19]
Fry

[11] Patent Number: 5,815,276
[45] Date of Patent: Sep. 29, 1998

[54] LONG-PATH ABSORBANCE-CELL IMAGING SYSTEM WITH DECREASED SYSTEM ELEMENT PARAMETER CHANGE BASED SENSITIVITY AND METHOD OF USE

[75] Inventor: Robert C. Fry, Omaha, Nebr.

[73] Assignee: Transgenomic Inc., Omaha, Nebr.

[21] Appl. No.: 944,280

[22] Filed: Oct. 6, 1997

Related U.S. Application Data

[60] Provisional application No. 60/027,709 Oct. 11, 1996.

[51] Int. Cl.$^6$ .................................................. G01N 21/31
[52] U.S. Cl. .......................................... 356/437; 356/440
[58] Field of Search ..................................... 356/437, 440

[56] References Cited

U.S. PATENT DOCUMENTS

| | | |
|---|---|---|
| 4,501,969 | 2/1985 | Lymnoes . |
| 4,518,861 | 5/1985 | Krempl et al. . |
| 4,544,273 | 10/1985 | Berndt ...................................... 356/434 |
| 4,606,644 | 8/1986 | Gordon ..................................... 356/438 |
| 4,662,755 | 5/1987 | Aoki et al. ............................... 356/414 |
| 4,998,017 | 3/1991 | Ryan et al. . |
| 5,146,283 | 9/1992 | Parnoff et al. ........................... 356/246 |
| 5,173,742 | 12/1992 | Young ...................................... 356/319 |
| 5,291,265 | 3/1994 | Kebabian ................................. 356/246 |
| 5,299,068 | 3/1994 | Cohn et al. .......................... 356/437 X |
| 5,339,155 | 8/1994 | Partridge et al. ........................ 356/419 |
| 5,428,222 | 6/1995 | Alexay ................................ 356/437 X |

Primary Examiner—Vincent P. McGraw
Attorney, Agent, or Firm—James D. Welch

[57] ABSTRACT

A long-path absorbance-cell optical imaging system, appropriate for use in cold vapor mercury analysis, which long-path absorbance-cell optical imaging system achieves decreased internal reflection mediated system-element-parameter-change-based sensitivity in use, by appropriate placement of apertures, is disclosed.

24 Claims, 5 Drawing Sheets

LONG-PATH ABSORBANCE-CELL IMAGING SYSTEM WITH DECREASED SYSTEM ELEMENT PARAMETER CHANGE BASED SENSITIVITY AND METHOD OF USE

This application is a CIP of Provisional patent application Ser. No. 60/027,709 filed Oct. 11, 1996.

TECHNICAL FIELD

The present invention relates to analytical chemistry, analytical instruments and more specifically to long-path absorbance-cell optical imaging systems, such as employed in cold vapor mercury photometric analysis, which long-path absorbance-cell optical imaging systems achieve decreased reflection mediated system-element-parameter-change-based sensitivity in use, by appropriate application of apertures.

BACKGROUND

Long-path absorbance-cell mercury vapor absorbance photometer systems, in which a two-hundred-fifty-four (254) nanometer (nm), beam of light is caused to pass through a chemically reduced analyte, (eg. $Hg°$), containing sample head-space vapor, and undergo a decrease in intensity by interaction with present analyte vapors, are known. Perkin-Elmer Corp. and Leeman labs Inc., for instance, each provide long-path absorbance-cell systems which comprise short a focal length fused silica lens means to collimate, (ie. make parallel light rays), radiation from a mercury vapor lamp source, and cause said collimated radiation to pass through a medium bore (eg. typically four (4) to seven (7) millimeters i.d.), long-path (eg. one-hundred (100) to three-hundred (300) millimeters length), glass, (or other material), absorbance tube. In accordance with the Beer-Lambert, (ie. "Beer's Law"), Photometry equation, absorbance of the collimated radiation, of a known wavelength, (eg 254 nm), which occurs by passage of said radiation through a chemically reduced analyte, (eg. $Hg°$), containing sample head space vapor, (hereinafter referred to as "Hg vapor"), present in said long-path absorbance-cell is determinative of original sample liquid analyte, (eg. $Hg^{2+}$), content and concentration. Beer's Photometry law, $(A=a*b*c)$, dictates that the longer the long-path absorbance-cell pathway (b), the greater will be the absorbance (A) of radiation therein by vapor concentration (c). The transmitted light intensity follows an inverse exponential relationship with respect to long-path absorbance cell length (b), but a ratio of a transmitted intensity (I) value to original incident intensity (IO) value provides a linear relationship when mathematically operated on by well known negative logarithmic function to yield the well known resultant quantity termed the "optical absorbance" (A), where $(A=-Log(I/IO))$, said absorbance quantity (A) being linearly related to cell path length (b) and analyte concentration (c) according to well known Beer's law relationship $((A)=a*b*c)$, where (A) is a absorbance, (a) is a calibration coefficient, (b) is cell path length, and (c) is analyte concentration. It is to be understood that Long-path absorbance-cells are therefore beneficial in the analysis of drinking water, blood, urine, fish tissue and the like samples wherein an analyte, (eg. Hg), content is too low to register an accurate absorbance in a "short-path", (eg. one (1) to ten (10) millimeters long), absorbance-cell system. That is, for a fixed low concentration (c), increasing the known cell path length (b) increases the measured absorbance (A) according to said Beer's law $((A)=a*b*c)$.

Long-path absorbance-cell glass, (or other material), absorbance tubes are typically constructed with internal space-confining, ultraviolet transparent end-windows, (eg. made of fused silica, quartz or sapphire etc.), and include means for causing analyte, (eg. $Hg°$), containing sample vapor to flow therethrough in use. Absorbance photometer systems may comprise either "single beam", (ie. one long-path absorbance cell), or "double beam", (ie. comprising two identical long path absorbance cells), optical configurations. In modern "double-beam" configurations, simultaneous with the flow of sample vapor, a light beam of user determined wavelength, (eg. where mercury is the analyte, a wavelength of two-hundred-fifty-four (254) nanometers is utilized), and incident radiation intensity (IO) is caused to enter a first "sample" long path absorbance cell system component containing sample, (liquid or vapor), and also to enter an independent second "reference" long-path absorbance-cell system component, which contains only "blank" inactive carrier media used to propel the aforementioned sample vapors through said first said long-path absorbance cell component, (eg. the "sample" cell). Upon the transversing "sample-cell", the first emerging beam is of reduced intensity (I) relative to incident beam intensity (IO), because of absorption by, for example, a ($Hg°$) vapor. Upon transversing the "reference-cell", the second emerging beam is deemed to represent the incident beam intensity (IO), (during measurement simultaneous with measurement of said first emergent beam from said sample cell). Intensities, (ie. radiant powers), (I) and (IO) emerging from the two long-path absorbance-cell system components "sample" and "reference" are opto-electronically compared. Said opto-electronic comparison involves an inverting negative Log ratio comparison of light intensities of beams independently transversing sample, (eg. light intensity "I"), and reference, (eg. light intensity "IO"), long-path absorbance-cells allows evaluation of sample beam absorbance (A), where $(A)=-Log(I/IO)$. Thus measured absorbance (A) is further related to sample concentration by $((A)=a*b*c)$, where, again, (A) is a absorbance, (a) is a calibration coefficient, (b) is cell path length, and (c) is analyte concentration. Typical applications involve determining the concentration of an analyte vapor produced from an analyte, (eg. $Hg^{2+}$), containing liquid sample solution by first calibrating the system calibration coefficient (a) by passing a known concentration (c') standard analyte ($Hg^{2+}$) containing liquid sample solution through a stannous chloride reactor, (to produce $Hg°$ vapor), then through a gas-liquid separator to isolate said $Hg°$ vapor, then through a drying means for removing interfering water vapor, and then through a long path "sample" absorbance-cell system component. Said long path absorbance-cell system component being in the path of a monochromatic light beam of two-hundred-fifty-four (254 nm) namometers wavelength. The intensity (I') of said emergent beam being selectively attenuated via spontaneous atomic absorption by dry vaporous $Hg°$ contained in said long-path absorbance-cell system component, yielding an absorbance (A') equal to the negative Log ratio of initial beam intensity (IO) and attenuated beam intensity (I'), where $((A')=-Log(I'/IO))$. ((IO) being measured from the reference beam measurement in a "double beam" system or simply from sequentially obtained "blank" solution measurement in a "single beam" system). Said overall system being effectively calibrated for known $Hg°$ concentration (c') by measuring Beer's law correlation of said Absorbance (A') of said beam, with said known concentration (c') of mercury ($Hg^{2+}$) ins aid standard analyte containing original sample solution and computing system calibration coefficient (a) from the rearranged form of Beer's law, $(a=A')/b*c')$. In use said system calibration coefficient (a) is followed by passing an unknown "same analyte" (eg. ($Hg^{2+}$) concentration (c) containing sample solution through the same stannous chloride reactor, gas-liquid-separator, drying means and long-path absorbance-cell system component, (the purpose being to determine the ($Hg^{2+}$) concentration in said unknown by measuring its ($Hg°$) vapor transmitted intensity (I) and its ($Hg°$) absorbance (A), (as (A)=(I/IO), and computing solution concentration (c) from prior determined calibration coefficient (a), (evaluated above when the standard known concentration sample was passed therethrough), and known cell path length (b), by employing a further rearranged form of Beer's law (c=(A)/(a*b)).

It is noted where ($Hg^{2+}$) mercury is the analyte, vapor thereof ($Hg°$) is typically produced from liquid solution or solid sample by a process involving acidification, heating, oxidizing (including dissolution of any solids), and concinuous pumping of the resulting liquid into a flow-through statnnous chloride reactor, (or other chemical reaction reactor), where continuous chemical reduction occurs, (eg. ($Hg^{2+}$) reduced to ($Hg°$)), followed by a flow-through gas-liquid separation, and drying of said ($Hg°$) vapor. As mentioned, the stannous chloride reactor provides chemical reductant means which converts traces of dissolved ($Hg^{2+}$) to ($Hg°$), which is semi-volatile. The gas-liquid separator (GLS) evaporates the $Hg°$ into a carrier gas stream, and the dryer removes residual water vapor, (also produced to some extent during the $Hg°$ evaporation). Overall process conversion and transport efficiency is accounted for by the calibration coefficient (a) in Beer's law, ((A)=a*b*c), where, again, the calibration coefficient (a) is evaluated by measuring transmitted ($Hg°$) intensity (I') and absorbance (A') of known original ($Hg^{2+}$) reduced standard solution of known concentration (c') and the optical system is of known path length (b), by (a=(A')/(b*c')), and where ((A)=−Log (I'/IO)) and where reference intensity (IO) is measured simultaneously from a reference beam in a "double beam" system or sequentially from a "blank" solution in a "single beam" system measurement in a "single beam".

The text "Instrumental Methods Of Analysis", by Willard, Merritt, Jr., and Dean, D. Van Nostrand Co., 1974 is incorporated by reference hereinto as a source for the recited mathematics and further insight to the described technique for determining the concentration of an analyte in a liquid sample.

Continuing, it is to be understood that while long-path cold-vapor mercury absorbance-cell absorption photometry has proven to be capable of generating data of the highest accuracy heretofore possible, regarding low mercury concentrations in liquid samples, (or mercury in air samples), several problems remain in the application of long-path absorbance-cell systems which presently exist for practice of said technique. For instance, even where a supposedly collimated beam of radiation is utilized, severe optical aberrations based in simple short focal length curved optical elements, (and large "non-point" source dimensions), result when portions of said collimated beam are inevitably imperfectly collimated and resulting aberrant diverging rays specularly, one or more times, reflect from cell-wall surfaces in a long-path absorbance-cell, then enter a detector by other than a direct collimated, (ie. parallel ray), transmission pathway through said long-path absorbance-cell. Intensities of unwanted specular reflections vary, for instance, with small changes in the orientation of, and surface characteristics of an internal reflective surface of, a long-path absorbance-cell, in use, whereas directly transmitted (unreflected) rays are not subject to said intensity variation, emphasis added. For instance, long-path absorbance-cell walls tend to get "dirty" in use causing detector intensity signal baseline drift, (owing to change in wall reflectance where unwanted reflected rays are concerned), or sudden baseline offsets to occur. As well, low-angle long-path absorbance-cell wall reflections are susceptible to detector intensity effecting change induced by thermally indirect offset or "twist" of said long-path absorbance-cell and/or a holder thereof. It is important to note that detector signals arising solely from directly transmitted, (unreflected), rays are far less susceptable to said signal baseline drift or offset component. It should be readily appreciated that changes in reflection mediated radiation intensity which are not derived from characteristics of an analyte concentration in a sample present in a long-path absorbance-cell cause errors in determination of said analyte concentration. And, said errors become particularly significant where samples in the ultr-low concentrations range of one-half (0.5) to fifty (50) parts per trillion, (which is equivalent to 0.0005 to 0.050 parts per billion of, for instance, mercury), are to be investigated. The magnitude of the problem is perhaps best described by realizing that approximately forty (40%) percent of a beam of "collimated" radiation passing through a seven (7) millimeter i.d. tubular glass cell of two-hundred-fifty (250) millimeters in length, and approximately seventy (70%) percent of nominally collimated radiation passing through a four (4) millimeter i.d. absorbance-cell of similar length is comprised on undesirable, imperfectly collimated, (eg. diverging rays) components which are specularly reflected from reflective internal surfaces of a long-path absorbance-cell, via the "light-pipe" effect. As the internal reflection properties of a surface of a long-path absorbance-cell vary, depending on surface properties and orientation in a long-path absorbance-cell absorbance photometry system, severe limitations regarding baseline drift, uncompensated offset and reliability of results provided, are attendant with use of existing long-path absorbance-cell absorbance photometry systems. In addition, due to said baseline drift and uncompensated offset, long-path absorbance-cell absorbance photometry systems are notoriously difficult to calibrate and stabilize, compared to short-path counterparts.

In view of the above, it should be apparent that a long-path absorbance-cell absorbance photometer system which provides means to eliminate the effects of aberrant reflection mediated radiation in a detector signal, would provide great utility. With this in mind, a search of Patents was performed. It is noted that as the present invention comprises appropriately positioned apertures, (as described in following Sections of this Disclosure), the presence of apertures which serve to selectively block reflection mediated radiation access to an intensity monitoring detector in a long-path absorbance-cell absorbance photometry system, was a particular focus of said Patent Search.

A Patent to Parnoff, U.S. Pat. No. 5,146,283 was identified and is disclosed as the system thereof includes a Frusto-conical shaped sample cell, the inner surfaces of which are provided absorption means, and in which are present apertures, though said apertures are not mentioned in the Claims. Primary prevention of reflected rays from reaching the detector is due to frusto-conical geometry. In the shown preferred embodiment the apertures appear to be secondarily involved and are implied means for preventing a residual minority portion of the reflected energy impinging on the sample cell from reaching the detector. Described are gas entry and outlet means disposed solely on the bottom of the system, as well as condensate removal means.

A Patent, U.S. Pat. No. 5,428,222, to Alexay was identified and is disclosed because it describes a Non-Imaging Optical Member (14) which serves to direct rays, at a reduced angle, into a sample cell detector. Structural relevance of the Alexay invention is minimal and critical apertures are not employed.

U.S. Pat. No. 4,662,755, to Aoki et al., is also disclosed as it includes Apertures (6), and a moveable Detector (3). By changing the distance said etector is located from the Apertures, or the size of the apertures, one can focus upon a wavelength of interest which defines an angle of incidence light rays make with respect to an inner cell surface. Said apertures are not utilized to eliminate wall reflection, but rather mirrored surface wall reflection is deliberately included and said apertures serve only to define maximum included reflection angle and to effect fine shift in central wavelength value transmitted by filters.

U.S. Pat. No. 4,544,273, to Berndt, includes a plurality of Apertures (50) for use in collimating a light beam. At least one Aperture is present at the Input of the Light Beam to a Tube, and a second is present at the outlet of said tube. However, said aperatures are not placed at any particular object plane or focal plane of any particular optic. In particular there is no optic after the absorbance cell to directly focus unwanted reflections onto an image plane where limiting aperture is available to positively remove them by selectively masking of any optically defined image, of which there is none.

U.S. Pat. No. 5,339,155 to Partridge et al. also shows an a primary Aperture (24) in a Long-Path Gas Monitoring System, but said aperture is not in the collimated portion of the beam and it does not serve to remove reflections.

A U.S. Pat. No. 5,173,742, to Young shows a Double Beam Detector, in which Apertures are present, (38) as well as Cell Bores (48) & (47).

U.S. Pat. No. 5,299,068 to Cohn et al. describes a Nuclear Radiation Source and a laser, and Apertures (18).

U.S. Pat. No. 5,291,265 to Kebabian shows an Off-Axis Cavity Absorption Cell system with an Aperture (24) at the input end thereof. A Mirror is present at the other side, rather than another Aperture in an Image Plane.

U.S. Pat. No. 4,998,017 to Ryan et al. shows an Aperture (34). U.S. Pat. No. 4,50,969 to Lymnoes shows an Aperture (4). U.S. Pat. No. 4,606,644 to Gordon show plurality of Apertures. U.S. Pat. No. 4,518,861 to Krempl et al. shows Apertures (21) and (28).

No system in any known reference, however, describes a system for essentially eliminating the effects of aberrant reflection mediated radiation in the context of a long-path absorbance-cell absorbance photometry system. A need remains for such an internal aberrant specular reflected radiation effect minimizing system, and method(s) of use.

DISCLOSURE OF THE INVENTION

The present invention is an optical imaging system for use in long-path absorbance-cell absorbance photometry, which optical imaging system demonstrates decreased sensitivity to internal wall reflection mediated system element parameter change in use. The present invention can also be considered as a system for selectively masking reflection mediated components of a light beam passed therethrough in use.

Said present invention optical imaging system consists of at least one optical imaging system component, each of which at least one optical imaging system component(s) sequentially comprises as elements:

a light source;
a backlighted primary limiting field stop;
an essentially tubular shaped long-path absorbance-cell;
a secondary focusing optic;
a secondary field stop; and
a light intensity detector system.

Also typically present is a collimator optic, which in combination with said light source, serves to provide essentially collimated rays to said backlighted primary limiting field stop. Said collimator optic can be, for instance, a lens placed between said light source and said backlighted primary limiting field stop with said light source at its focal point, or other than a lens, (eg. an on-axis or off-axis convex mirror or mirror system positioned with said light source at its focal point so as to direct parallel essentially collimated rays to said backlighted primary limiting field stop). As well, it is to be understood that each of the backlighted primary limiting field stop and the secondary field stop has present therein an aperture. In addition, the terminology "essentially tubular" is to be interpreted to require only that a bore be present through an essentially tubular shaped long-path absorbance-cell, through which bore essentially collimated light can pass in use. This implies no limitation on the cross-sectional shape of said bore, or a relationship between said cross-sectional bore shape and an outer dimension cross-section shape of an essentially tubular shaped long-path absorbance-cell.

Exemplary, non-limiting, dimensions of typical present invention optical imaging system component elements are:

a. backlighted primary limiting field stop aperture diameter—0.118 inches inner diameter (i.d.).
b. secondary field stop aperture diameter—0.052 inches i.d., (note that said secondary field stop aperture is nominally placed at a 4.3X image reduction plane, (coresponding to a magnification of 0.23), of the secondary focusing optic, which secondary focusing optic is positioned so as to have said backlighted primary limiting field stop aperture, as object),
c. essentially tubular shaped long-path absorbance-cell length—100 to 300 millimeters long.
d. essentially tubular shaped long-path absorbance-cell diameter—0.259 inches i.d., (which it is to be noted is greater that the backlighted primary limiting field stop aperture i.d. of 0.118 inches).

where more than one optical imaging system component is present, simultaneous wide beam "back illumination" of two primary limiting field stop apertures can be from a single source wide beam collimating optic, and the resulting multiple component optical imaging system components can be spaced, for instance, with optical imaging system component center lines spaced approximately 0.616 inches apart.

The essentially tubular shaped long-path absorbance-cell comprises an inner essentially tubular diameter, essentially transparent and windows, and means by which to cause an analyte containing sample to enter and pass therethrough in use. It is instructive to realize that ideally, the present invention light source should provide a perfectly collimated base of light to said backlighted primary limiting field stop, and a reduced diameter beam of light exiting said backlighted primary limiting field stop aperture would also be perfectly collimated. In practice however, light sources are not capable of providing perfectly collimated beams of light, and all known collimation optics, (especially short focal length, single element spherical optics), which are followed by passage through an aperture, introduce aberration(s) of one sort or another into a light beam caused to pass therethrough. It is the effects of the presence of reflections of such "aberrant" components of a beam of otherwise essentially collimated light entered to a present invention essentially tubular shaped long-path absorbance-cell, said reflection being from an internal surface of said essentially tubular shaped long-path absorbance-cell, and changes in said reflections based upon reflection mediated physical changes in a system including a present invention essentially tubular shaped long-path absorbance-cell, which the present invention system serves to selectively mask. It is to be understood that the effects of uncompensated changes in the identified reflection of aberrant components of an essentially collimated light beam utilized in an absorbance cell, are a major source of error in analyte presence and concentration measurements in practice, emphasis added. And, it is said source of error which the present invention essentially eliminates. The significance of this can be appreciated by noting that up to thirty (30%) percent or more of the intensity measured in typical long-path absorbance-cell based systems sample analysis systems can be the result of multiply reflected aberrant components in an essentially collimated light beam, emphasis added. A present invention long-path absorbance-cell based system, it should be understood, allows achievement of detection limits which are on the order of ten-to-the-minus-fifth absorbtion units, or better, regarding uncompensated reflection mediated intensity drift, (ie. where change greater than 0.0025% of reflected light intensity is significant). In prior art systems in which reflections are allowed to pass to an associated detector system, much larger, (eg. ten (10) to twenty (20) times larger), reflection mediated changes occur, and thereby prevent achievement of ten-to-the-minus-fifth absorbance detection limits. It is to be understood that higher, (ie. worse), absorbance detection limits mean that analyte (eg. mercury), concentration detection limits are higher, (ie. worse), as well.

Continuing, it is to be understood that a typical analyte containing sample will be in a liquid or vapor form, and the present invention essentially tubular shaped long-path absorbance-cell is configured to allow entry thereof and essentially confine such therein during throughflow, in use. Also, as exemplified infra herein, said backlighted primary limiting field stop aperture inner diameter is smaller than the inner essentially tubular diameter of said essentially tubular shaped long-path absorbance-cell, and in use said backlighted primary limiting field stop aperture is positioned such that it is essentially centrally located with respect to a relatively larger inner essentially tubular diameter first light source illuminated end of said essentially tubular shaped long-path absorbance-cell. The backlighted primary limiting field stop in use, causes a light source initiated small diameter beam formed by passage through said backlighted primary limiting field stop aperture, to, as an essentially centrally located essentially collimated beam, (via said essentially transparent end windows), enter, proceed through, and then exit said essentially tubular shaped long-path absorbance-cell at an end thereof distal to said first light source illuminated end thereof. The result is that the essentially collimated beam emerging from the center of said backlighted primary limiting field stop aperture, (said collimated beam consisting of rays emerging from said backlighted primary limiting field stop aperture), when caused to pass through said essentially tubular shaped long-path absorbance-cell, and emerge therefrom, are essentially unaffected by reflection(s) of aberrant components of said small diameter essentially collimated beam from an inner wall thereof, emphasis added. It must also be appreciated that aberrant specular reflections illuminate interior tubular walls of an essentially tubular shaped long path absorption-cell, and it is disclosed that the backlighted primary limiting field stop aperture simultaneously casts a plurality of reflected concentric dark shadow-rings of progressively increasing diameter interior to said essentially tubular shaped long-path absorbance cell, and onto the inner wall of said essentially tubular shaped long path absorbance cell, said dark shadow-rings discontinuously interrupting said interior wall aberrant specular reflection illumination to produce a series of concentric specular reflection light halo-rings interrupted by, and interspersed with, dark shadow-rings. Said dark shadow-rings are present surrounding said essentially collimated center beam component which consists of unreflected rays originating from said backlighted primary limiting field stop aperture. It is noted that said dark shadow-rings and light halo-rings are viewable through said end of said essentially tubular shaped long-path absorbance-cell distal to said first light source illuminated end thereof. It is of interest to not that without the backlighted primary limiting field stop aperture in place, such an observation provides a generally continuous "gleam" much as viewed when looking down the inside of a barrel of a gun with an opposite end thereof open to light. Said continuous barrel gleam is due to uninterrupted specular reflection. It is then the presence of the backlighted primary limiting field stop aperture in place, as described, in the present invention system which serves to "break-up" said essentially continuous "gleam" into a plurality of "quantized" dark shadow-rings and interspersed aberrant light halo-rings, and it is the described effect, (and subsequent selective masking thereof), which is at the heart of the operation of the present invention.

Continuing, it is disclosed that each of said dark shadow-rings demonstrates substantial ring band thickness and has defined edge boundaries. It is further disclosed that said dark shadow-ring thicknesses vary inversely with the inside diameter of said backlighted primary limiting field stop aperture diameter and directly with the inner diameter of said essentially tubular shaped long-path absorbance cell. Again, said dark shadow-rings are separated from one another by interspersing aberrant ray, reflection effected, light halo-rings. With respect to the present invention, it is disclosed that a very important point is that the outer diameter of an essentially centrally located small diameter secondary optic focused spot image effecting essentially collimated beam at the location of the secondary field stop aperture, is less than that of all but an innermost of said dark shadow-rings and less than all of said aberrant ray reflection effected light halo-rings. Continuing, said secondary focusing optic is situated pas the end of said essentially tubular shaped long-path absorbance-cell, which is distal from the first light source illuminated end thereof, and prior to said secondary field stop, with the location of said secondary field stop being situated in the vicinity of the image plane of said secondary focusing optic where the location of said backlighted primary limiting field stop aperture is taken as the secondary focusing optic object distance in the well known optic formulas:

$$(1/O)+(1/I)=(1/F), \text{ and}$$

$$M=I/O;$$

where "O" is the object distance from said secondary focusing optic to said backlighted primary limiting field stop aperture; "I" the image distance from said secondary focusing optic to said secondary field stop, and "F" is the focal length of said secondary focusing optic, and "M" is the image magnification ratio. The relative magnitudes of "O", "F" and "I" are typically selected to render "M" small, (eg. less than 0.25), and the depth of focus of said secondary focusing optic sufficiently large, (regarding "object" focus), to encompass said primary backlighted field stop and all observed shadow-rings and all interspersed reflection effected light halo-rings. In use, the secondary field stop aperture is concentrically positioned to allow passage of a secondary focusing optic focused essentially centrally located, substantially demagnified, (eg. "M"=0.23), spot image of said backlighted primary field stop effecting small diameter essentially collimated beam therethrough, and entry thereof into said light intensity detector system. Most importantly, however, it is to be understood that said inner diameter of said secondary field stop aperture is smaller than that of any of secondary focusing optic focused aberrant beam component reflection effected concentric light halo-rings, such that none of said light halo-rings are passed by said secondary field stop aperture, emphasis added.

To demonstrate, typical dimensions of a centrally located spot image, an innermost Dark Shadow-ring, and a first concentric light halo-ring in a present invention optical imaging system are:

| | |
|---|---|
| a. centrally located demagnified, ("M" = 0.23), spot image | 0.028 inches o.d. |
| b. secondary field stop aperture | 0.052 inches i.d. |
| c. first concentric light halo-ring image | 0.076 inches i.d. |
| d. first dark shadow-ring | 0.028 inches i.d. |
| | 0.076 inches o.d. |

This demonstration shows that with diameter difference (0.024 inches), giving rise to a radius difference of (0.012 inches), there is a typical 0.012 inch radius gap between the outer diameter, (0.028 inch), of a centrally located spot image and the inner diameter, (0.052 inch), of concentrically positioned secondary field stop aperture. (Note that said dimensions reveal that said 0.012 inch radius gap is within said innermost dark shadow). There is an additional (0.012 inch) gap between said inner diameter of said concentrically positioned secondary field stop aperture and a concentrically oriented inner diameter of the first light beam aberrant component reflection effected light halo-ring. (Again, said dimensions reveal that said gap occurs within said innermost dark shadow). It is further to e understood that change of long-path absorbance-cell temperature from room temperature to ninety (90) degrees centigrade, (said temperature change typically being induced by a long-path absorbance-cell "oven" heater means utilized to prevent Hg° vapor condensation in said cell), effects theremally induced dimension changes which are on the order of a relatively small 0.002 inch. It should then be appreciated that the outer diameter, (0.028 inches), of the centrally located spot image is immediately surrounded by darkness, and is furthermore relatively significantly smaller than is the inner diameter of the secondary field stop aperture diameter, which, as was provided infra herein, is typically 0.052 inches. However, and most importantly, said secondary field stop aperture is surrounded by yet more darkness beyond its inner diameter dimension, and said inner diameter is relatively significantly smaller than is the inner diameter, (0.075 inches), of the first concentric light halo-ring, and all larger concentric light rings consisting of aberrant specular reflection beam components. And again, typically experienced thermal motions over a reasonable temperature range do not adversely affect said identified relative diameter relationships, (ie. the centrally located spot image passes through the secondary field stop aperture, but no reflected aberrant ray effected light halo-rings do so, in spite of thermally induced motion of 0.002 inches). Even when said 0.002 inch thermally induced motion is combined with typical manufacturing and location tolerances totalling 0.006 inches, it should be appreciated that the 0.012 inches margin of error allowed for "drift" immunity is not exceeded in any direction of reflection.

The result being that said essentially tubular shaped long-path absorbance-cell element parameters can change during use, resulting in changes in location of said plurality of reflected concentric dark shadow-rings of progressively increasing diameter and interspersing light halo-rings, without affecting the essentially centrally located backlighted primary limiting field stop aperture spot image, (present as an essentially collimated beam), effected reading of said light intensity detector system.

In the described present invention system it is to be understood that the focal length (F) of the secondary focusing optic, present between said essentially tubular shaped long-path absorbance-cell and said secondary field stop, is preferably selected to be sufficiently small that the real image distance (I) is relatively short, (eg. near said focusing lens), so as to produce substantial image demagnification, (ie. small magnification ratio "M", (eg. 0.23), which is the ratio of small image distance to large object distance). This is accompanied by a substantially large depth of focus of said focusing lens, as regards the object (O), (ie. the backlighted primary limiting field stop). The object plane depth of focus is typically, however, sufficiently large to encompass the backlighted primary limiting field stop and the first illuminated extent of the essentially tubular shaped long-path absorbance cell, including all aberrant "gleam" which is interspersed with concentric dark shadow-rings. The important thing to not being tha, in use, the essentially collimated beam backlighted primary limiting field stop aperture spot image at said secondary field stop aperture is ultimately left essentially separated from, independent of, and unaffected by reflection(s) of aberrant components of said small diameter essentially collimated beam, which aberrant rays reflect from an inner wall surface within said essentially tubular shaped long-path absorbance-cell. Again, said reflection mediated aberrant rays are selectively removed by said secondary field stop, during passage of said isolated essentially collimated beam spot image through said secondary field stop aperture, prior to reaching a detector.

It is noted that the light intensity detector system can include a wavelength isolating/selecting means, such as a filter, grating, prism or interferometer etc., prior to an active intensity measurement effecting detector element therein. It is further noted that an alternative configuration would allow positioning of said wavelength isolating means prior to said backlighted primary field stop aperture, or even prior to said collimating optic, and still be within the scope of the present invention.

It is also noted that the shape of the inner bore of the essentially tubular shaped long-path absorbance-cell is typically chosen to be essentially circular and constant over the length thereof, between first light source illuminated end of said essentially tubular shaped long-path absorbance-cell, and said end of said essentially tubular shaped long-path absorbance-cell distal to said first light source illuminated end thereof. However, other shapes, such as essentially oval, essentially elliptical, essentially square and essentially rectangular etc. are within the scope of the present invention, and an effective tubular inner diameter of a bore can also vary over said length range.

It is also noted that an inner surface of said essentially tubular shaped long-path absorbance-cell can be caused to be nonreflective and be within the scope of the present invention. This, however, is not a limitation on the present invention and is not necessarily a reliable approach to achieving the effect provided by the present invention, because at sufficiently low angle, even the most "nonreflective" surface can undergo "total internal reflection" as evidenced by well known "highway-mirrage" effects on a mid-summer's day, and because accumulating dirt etc. can change reflectance properties of an inner surface of an essentially tubular shaped long-path absorbance-cell, over time.

It is also noted that a typically preferred embodiment of the present invention provides that two optical imaging system components be present and comprise a "double beam" absorbance photometer system. The reason for this will be appreciated supra herein. However, a "single beam" absorbance photometer system comprising above described elements is also within the scope of the present invention.

Most essentially, the present invention system is then an optical imaging system for use in long-path absorbance-cell absorbance photometry. Said optical imaging system demonstrates decreased sensitivity to internal wall reflection mediated system element parameter change in use and said optical imaging system consists of at least one optical imaging system component, each of which at least one optical imaging system component(s) sequentially comprises as elements:

a light source;
a backlighted primary limiting field stop;
an essentially tubular shaped long-path absorbance-cell;
a secondary focusing optic;
a secondary field stop; and
light intensity detector system.

Said backlighted primary limiting field stop and secondary field stop each comprise an aperture. Said backlighted primary limiting field stop is placed at a distance essentially equivalent to the object distance of said secondary focusing optic away from said secondary focusing optic to one side of said secondary focusing optic, and said secondary field stop being placed in the vicinity of focal plane of said secondary focusing optic on an optically opposite side of said secondary focusing optic. The aperture in said secondary field stop is placed where a focused, (typically, but not necessarily demagnified), spot image of said backlighted primary limiting field stop aperture appears in use, when an essentially collimated beam of light, originating at said light source, is caused to pass through said aperture of said backlighted primary limiting field stop and said essentially tubular shaped long-path absorbance-cell. As described infra herein, said focused spot image of said backlighted primary limiting field stop aperture demonstrates decreased sensitivity to internal wall reflection mediated system element parameter change because essentially only essentially collimated beam components which do not undergo reflection from internal walls of said essentially tubular shaped long-path absorbance-cell appear thereat, and are focused to an extent sufficiently small to pass through an appropriately placed, appropriate diameter, secondary field stop aperture.

A method of practicing "single beam" long-path absorbance-cell photometry comprises the steps of:

a. providing an optical imaging system for use in long-path absorbance-cell absorbance photometry, as described infra herein and, in a functional order, performing the further steps of:

b. causing a blank carrier medium without analyte content to pass through an essentially tubular shaped long-path absorbance-cell;

c. simultaneous with step b., causing a beam of light from a light source to pass through and exit a backlighted primary limiting field stop aperture associated with an essentially tubular shaped long-path absorbance-cell, said essentially tubular shaped long-path absorbance-cell, and an aperture of an associated secondary field stop, then enter a detector system wherein the intensity, at desired wavelength(s), thereof is determined;

d. causing a light absorbing analyte containing known concentration standard sample to pass through the same essentially tubular shaped long-path absorbance-cell;

e. simultaneous with step d., causing a beam of light from a light source to pass through and exit said backlighted primary limiting field stop aperture associated with said essentially tubular shaped long-path absorbance-cell, said essentially tubular shaped long-path absorbance-cell, and said aperture of said secondary field stop, then enter said detector system wherein the intensity, at desired wavelength(s), thereof is determined;

f. causing a light absorbing analyte containing unknown concentration sample to pass through the same essentially tubular shaped long-path absorbance-cell;

g. simultaneous with step e., causing a beam of light from said light source to pass through and exit said primary limiting field stop aperture associated with said essentially tubular shaped long-path absorbance-cell, said essentially tubular shaped long-path absorbance-cell, and said aperture of said secondary field stop, then enter said detector system wherein the intensity, at desired wavelength(s), thereof is determined;

h. comparing the light intensity results determined in steps c., e. and g. and computing absorbance from photometry laws; and i. from the comparison in step h. and and the known standard sample concentration, determining the analyte content of said unknown analyte containing sample caused to pass through said essentially tubular shaped long-path absorbance-cell in step f.

Where more than one optical imaging system component is simultaneously available a "double-beam" photometer method of use can comprise, in a functional order, the steps of:

a. providing a double beam optical imaging system comprising two optical imaging system components for use in long-path absorbance-cell absorbance photometry, as described infra and, in a functional order, performing the further steps of:

b. sequentially causing a light absorbing analyte containing known concentration standard sample, and a light absorbing analyte containing unknown concentration sample to pass through a first essentially tubular shaped long-path absorbance-cell;

c. simultaneous with step b., causing a beam of light from a light source to pass through and exit a primary limiting field stop aperture associated with said first essentially tubular shaped long-path absorbance-cell, said first essentially tubular shaped long-path absorbance-cell, and an aperture of an associated secondary field stop, then enter a detector system wherein the intensity, at desired wavelength(s) for sequentially present samples, thereof is determined;

d. simultaneous with step b. causing a blank carrier medium without analyte content present therein to pass through a second essentially tubular shaped long-path absorbance-cell;

e. simultaneous with step d., causing a beam of light from said light source to pass through and exit a backlighted primary limiting field stop aperture associated with said second essentially tubular shaped long-path absorbance-cell, said second essentially tubular shaped long-path absorbance-cell, and an aperture of an associated secondary field stop, then enter a detector system wherein the intensity, at desired wavelength(s), thereof is determined;

f. comparing the light intensity results determined in steps c. and e. and computing absorbance values from photometry laws; and g. from the comparison in step f., and the known standard sample concentration, determining the analyte content of said analyte containing unknown sample caused to pass through said essentially tubular shaped long-path absorbance-cell in step b.

(Note, it is common practice, by those skilled in the art, to refer to said first and second essentially tubular shaped long-path absorbance-cells as "sample" and "reference" cells).

(Note also, that where a present invention system has been precalibrated, the procedure in the above recited methods involving causing a known concentration standard sample to flow through an essentially tubular shaped long-path absorbance-cell, can be eliminated, and thus becomes optional).

This latter method, it is noted, allows for compensation of light source drift during data acquisition using the data from the second essentially tubular shaped long-path absorbance-cell.

It is noted that typically one light source will be utilized to provide essentially collimated light beam to all present essentially tubular shaped long-path absorbance-cell components in single and multiple essentially tubular shaped long-path absorbance-cell component systems. This is not a limitation of the present invention however. As well, comparison of light intensities as identified infra. herein, in exemplary methods of use steps, typically are carried out between data obtained at identical wavelengths, (eg. two-hundred-fifty-four (254) nanometers where analysis for mercury is performed).

Also, it is to be noted that alternative double-beam embodiments of the present invention are possible wherein a single detector, two (2) and preferably four (4) apertures, a pair of beam splitters, (one each before and after a long-path absorbance-cell), a pair of auxiliary reflecting mirrors, (one each before and after a second light path absorbance-cell) and a pair of synchronized chopper wheels comprise a "double-beam-in-time" system. Alternatively the beam splitters and synchronous chopper wheels can be replaced by a pair of rotating half-silvered mirrors, (one half reflective and the other half transparent). Use of the present invention optical imaging system for use in long-path absorbance-cell absorbance, is within the scope of the present invention.

The present invention will be better understood by reference to the Detailed Description Section of this Disclosure, with appropriate reference to the accompanying Drawings.

SUMMARY

It is therefore a primary purpose of the present invention to provide a system for essentially eliminating the effects of aberrant specular, (also termed "light-pipe" or "barrel-gleam"), reflection mediated radiation on detector measured intensity in long-path single and double-beam absorbance-cell absorbance photometry, spectrometry and spectrophotometry systems.

It is another purpose of the present invention to provide a system which serves to reduce detector measured intensity base-line drift and sudden reflection caused artifact offsets in long-path absorbance-cell absorbance photometry systems in use.

It is still yet another purpose of the present invention to provide a system which serves to reduce the need to frequently clean inner reflecting walls in long-path absorbance-cell absorbance photometry system absorbance cells.

It is yet still another purpose of the present invention to provide a system which serves to increase reliability and reproducibility of ultra-low level analyte analysis in long-path absorbance-cell absorbance photometry systems, particularly where mercury is the analyte.

It is a further purpose of the present invention to provide a system which meets the foregoing purposes, which system is easy to manufacture, install, calibrate, maintain and service.

It is another purpose of the present invention to provide methods of use of said system which meets the foregoing purposes.

BRIEF DESCRIPTION OF THE DRAWINGS

FIG. 2b shows an expanded scale detail of the backlighted primary limiting field stop (PFS) region of the present invention essentially tubular shaped long-path absorbance-cell system (LPAC), identified in FIG. 2a.

FIG. 2c shows an expanded scale detail of the focusing lens (FL) and secondary field stop (SFS) region of the present invention essentially tubular shaped long-path absorbance-cell system (LPAC), identified in FIG. 2a.

FIG. 2d shows an expanded scale detail of the, secondary field stop (SFS), filter (FIL) and detector (DET) region of the present invention essentially tubular shaped long-path absorbance-cell system (LPAC), identified in FIG. 2a.

DETAILED DESCRIPTION

Figure 1A:
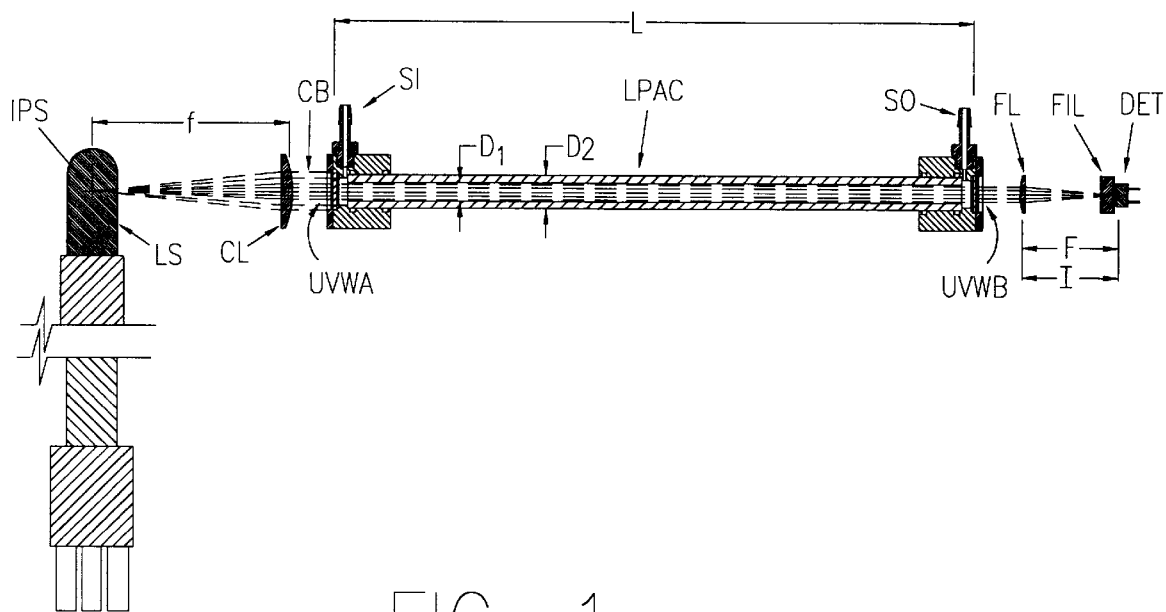
FIG. 1a. shows a side elevational cross section of a prior art long-path absorbance-cell system, with ideally collimated rays from a hypothetical ideal point source (IPS) centrally located optical on-optical-axis within a bulb of light source (LS), and located at a distance "f" from the collimating lens (CL), where "f" is the focal length of said collimating lens (CL).
Figure 1B:
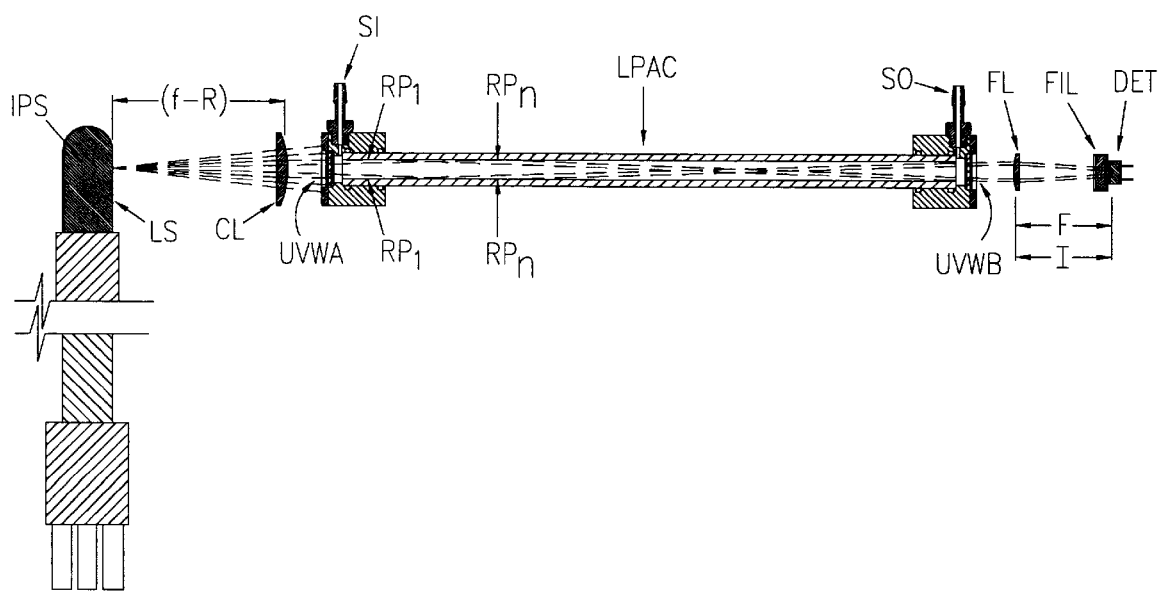
FIG. 1b shows a side elevational cross section view of a prior art long path absorbance cell system with real light source (LS) bulb extended in depth (D), hence deviating from an ideal point source.

Turning now to the Drawings, there is shown in FIG. 1a, a prior art single beam optical imaging system sequentially comprising a Light Source (LS), a Collimating Lens (CL), an essentially tubular shaped Long-Path Absorbance-Cell (LPAC), a Secondary Focusing Optic (FL) and a Detector System (DET). In the case where mercury is the analyte to be detected, said Light Source (LS) is typically a Mercury-Argon Discharge Lamp, and a two-hundred-fifty-four (254) nanometer Wavelength Selection Means (FIL), (eg. a Filtern, Grating, spectrometer, acusto-optic-tunable-filter, interferometer, prism, prism spectrometer, etalon, a wavelength specific or descriminating detector (eg. RGB), or functional equivalents and combinations thereof), can be added between the Secondary Focusing Optic (FL) and Detector (DET). Alternatively, said Wavelength Selection Means (FIL) can be located between said Light Source (LS) and said first light source lighted end of said essentially tubular shaped Long-Path Absorbance-Cell (LPAC), or in fact at any location in a present invention system through which an essentially Collimated Beam (CB) passes in use. Continuing, it should be noted that said essentially tubular shaped Long-Path Absorbance-Cell (LPAC) is shgown with internal space confining ultraviolet transparent windows (UVWA) and (UVWB) at left and right side ends thereof respectively, and Sample-In (SI) and Sample-Out (SO) Ports present which sequentially provide unknown sample, standard sample or blank sample, (ie. carrier media without analyte content), access to the space present inside thereof. Note that Ultraviolet transparent window (UVWA) is located at a first light source illuminated end of said essentially tubular shaped Long-Path Absorbance-Cell (LPAC), and Ultraviolet transparent window (UVWB) is present at a distal end thereof. Essentially tubular shaped Long-Path Absorbance-Cell (LPAC) is also shown to be of a length "L", and is shown with inner (D1) and outer (D2) tubular diameters. In use, an analyte containing sample, (eg. mercury vapor from an air sample or from a stannous chloride liquid reactor and gas-liquid separator (GLS)), is caused to be entered at Sample-In (SI) Port, proceed through the space within said essentially tubular shaped Long-Path Absorbance-Cell (LPAC), and exit via Sample-Out (SO) Port. Simultaneous therewith narrow-band electromagnetic radiation of user determinable wavelength content, (eg. 254 nm), and intensity is caused to be provided by Light Source (LS), (eg. a mercury lamp), proceed through Collimating Lens (CL) and become an essentially Collimated Beam (CB) consisting of essentially parallel, or long-path, rays. It is noted that ideally said Light Source (LS) is a point source located centrally, and on-axis, within a bulb, (see FIG. 1a). A portion of said essentially Collimated Beam (CB) is caused to travel through said essentially tubular shaped Long-Path Absorbance-Cell (LPAC) and pass through said Secondary Focusing Optic (FL). Said Secondary Focusing Optic (FL) serves to focus said essentially Collimated Beam (CB) at said Detector System (DET), which Detector System (DET) is located in a plane at a distance from said Secondary Focusing optic (FL) corresponding to the Focal Length (F) of said Secondary Focusing Optic (FL). It is noted that the image at said Detector (DET) is typically an image of the Light Source (LS), (eg. mercury lamp). It is again noted that a Wavelength Selection Means (FIL), (eg. 254 nm), is typically placed between said Secondary Focusing Optic (FL) and said Detector (DET), but could be positioned between said Light Source (LS) and said essentially tubular shaped Long-Path Absorbance-Cell (LPAC). As said Collimated Beam (CB) passes through said essentially tubular shaped Long-Path Absorbance-Cell (LPAC), mercury vapor analyte present therein serves to absorb energy from wavelengths, (eg. 254 nm), which are absorbed by said analyte. By knowing the intensity of the ideal Collimated Beam (CB) both prior to, and after, passage through said essentially tubular shaped Long-Path Absorbance-Cell (LPAC), one can theoretically determine the presence and concentration of analytes, (eg. Hg°), present in said essentially tubular shaped Long-Path Absorbance-Cell (LPAC). As well, by determining a Detector System (DET) provided intensity reading when a standard analyte containing sample is passed through said Long-Path Absorbance-Cell (LPAC), and a Detector System (DET) intensity reading when an unknown analyte containing sample is passed through said long-Path Absorbance-Cell (LPAC), and by then comparing said readings, (utilizing an intermediary intensity obtained when passing a blank through said Long-Path Absorbance-Cell (LPAC), one can calibrate said overall system as described in the Background Section of this Disclosure), and then determine the analyte content of said unknown sample. Note however that no real light source (LS) is ever "ideal". As shown by FIG. 1b, non-ideal rays from a "real" Light Source (LS) can originate from point (f-R) from the lamp edge nearest said Collimating Lens (CL), (ie. displaced from ideal point source (IPS) cente rpoint originated rays). Said real-world Light Source (LS) is then "extended in depth". Continuing, said non-ideal ray origination point (f-R), and many points between (f) and (f-R), give rise to aberrant non-collimated rays emerging from said collimator lens (CL) as eiverging rays, (as shown in FIG. 1b), according to the well known lens equation:

$$1O+1/I=1/F.$$

(Note that the identifiers (RP1) and (RPn) indicates that "n" reflection points for various diverging rays from an inner surface of said FIG. 1b essentially tubular shaped Long-Path Absorbance-Cell (LPAC) will exist in practice, said reflection points being positioned depending on where, in a Light Source (LS), a reflected ray originates).

The identified formula yields a mathematical solution Image "I" at Infinity, (ie. corresponding to unfocused, parallel rays), only in the special case where Object "O" distance in said lens formula exactly equals the Focal Length "F" of said collimator lens (CL). Thus it is clear that rays originating from non-ideal points located at various Object Distances "O", (less than the Focal Length "F" of said collimator lens (CL), cannot simultaneously provide Image rays at Infinity. The reason said non-ideal aberrant diverging rays (see FIG. 1b), are shown and discussed is to demonstrate that any prior art "collimated beam" component, (see FIG. 1a), transversing a long path essentially tubular shaped absorbance Cell, without undergoing wall reflections will inevitably be accompanied by non-ideal aberrant rays which must specularly reflect, undesirably, from inner walls of said essentially tubular shaped Long-Path Absorbance-Cell, and thereby give rise to an apparent "barrel-gleam", or otherwise stated, a "light-pipe" effect. Other origins of aberrant rays which additionally contribute to "barrel gleam", (or light pipe effect), include "coma" aberration from rays originating off-axis to optical axis, (eg. horizontal), center line passing through (IPS), (for example rays originating from points above or below the (IPS) location in FIG. 1a), and spherical aberration of Collimator (CL). (Note that coma and spherical aberrations are not illustrated by the Figures, but that they simultaneously give rise to aberrant divergently rays that inevitably contribute to specular reflections from essentially tubular shaped Long-Path Absorbance-Cell (LPAC) walls). Internal specular reflections, (ie. "barrel-gleam"), and movement, (eg. thermally induced), of said essentially tubular shaped Long-Path Absorbance-Cell (LPAC) during use, give rise to severe spectrometer baseline "drift", because of exaggerated alteration of aberrant reflected ray and barrel-gleam component intensity by said small thermally induced movement of an (LPAC). This causes the intensity of the radiation entering the Detector System (DET) to vary during use, and causes the Detector System (DET) to monitor changes in intensity which are not related to absorption by analyte present in said essentially tubular shaped Long-Path Absorbance-Cell (LPAC). This is a major cause of baseline signal drift inaccuracy, and non-repeatability of results in Long-Path Absorbance-Cell (LPAC) utilizing systems, and, it is noted, said reflection/thermal motion induces drift which is not canceled or compensated by prior art double beam systems because the reflection cannot be adequately duplicated in both cells, and the cells will generally not exhibit identical thermal induced motion. Furthermore, reflection mediated baseline "drift" is additionally altered by time variant accumulation of dirt or wall contamination in a sample carrying Long-Path Absorbance-Cell (LPAC), which dirt or wall contamination can change reflectance properties of internal wall reflectivity, which effect is not duplicated in reference cell.

Figure 2A:
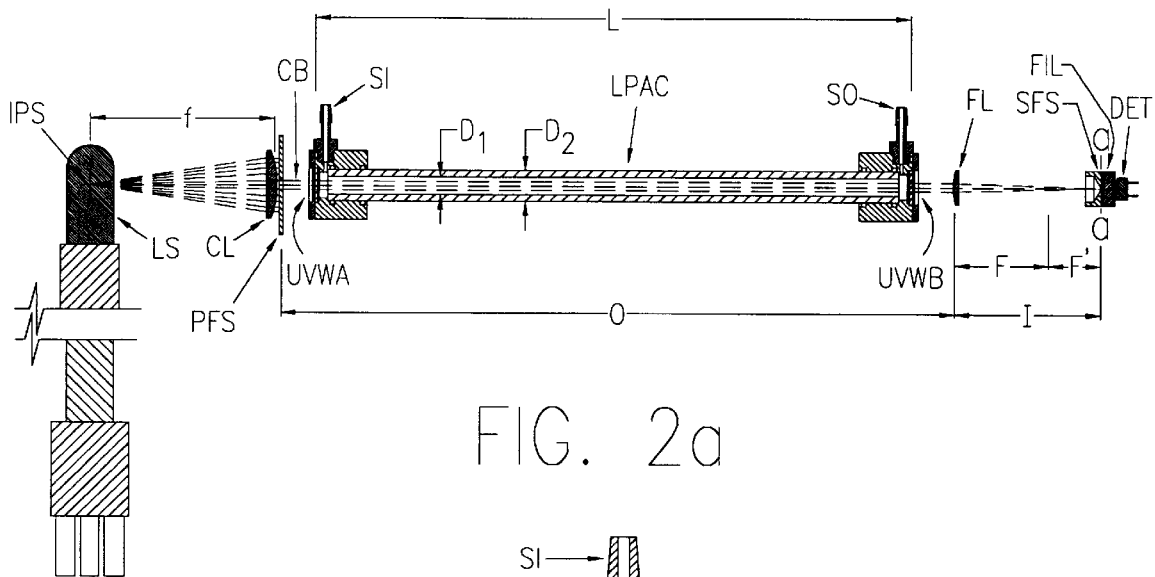
FIG. 2a shows a side elevational cross section of a present invention essentially tubular shaped long-path absorbance-cell system (LPAC) with backlighted primary limiting field stop (PFS), and secondary field stop (SFS) in position, including a lens (CL) collimating optic.
Figure 2B:
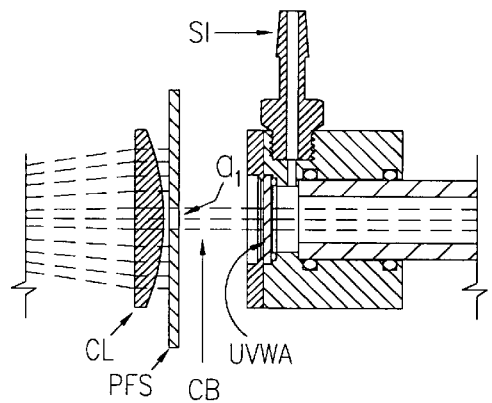
Figure 2C:
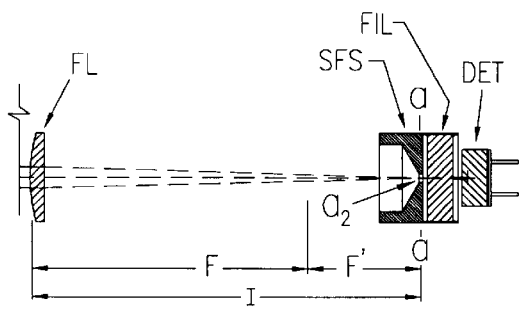
Figure 2D:
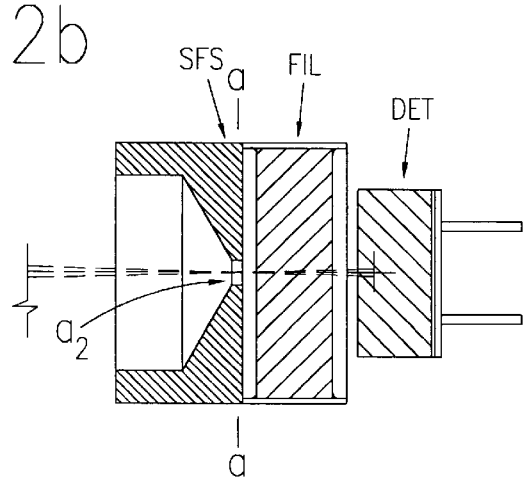
Figure 2E:
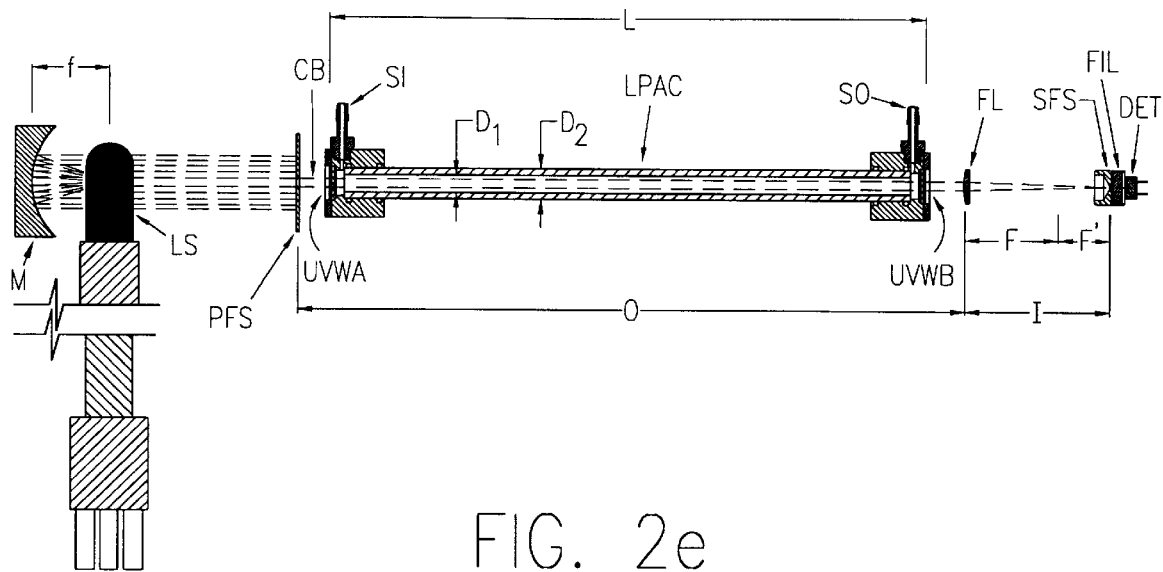
FIG. 2e shows a side elevational cross section of a present invention long-path absorbance-cell system (LPAC) with backlighted primary limiting field stop (PFS), and secondary field stop (SFS) in position, including a mirror (M) collimating optic.

Turning now to FIGS. 2a–2d, there is shown a Long-Path Absorbance-Cell Imaging System (LPAC) of the present invention. Note that Backlighted Primary Limiting Field Stop (PFS) which has an Aperture (a1) present therein, and a Secondary Field Stop (SFS) with an Aperture (a2) present therein have been added to the system of FIG. 1a, (see FIGS. 2a, 2c and 2d). Note that FIG. 2d shows an expanded scale detail of the FIG. 2a Secondary Field Stop (SFS), Secondary Field Stop (SFS) Aperature (a2), Wavelength Selection Means (FIL) and Detector (DET)), and that the Focal Plane of the Secondary Focusing Optic (FL) has been shifted by a distance identified as (F') from the focal plane shown in FIG. 1. That is, the Detector (DET) is no longer at the Focal Plane (F) of Secondary Focusing Optic (FL), but instead the Secondary Field Stop (SFS) Aperture (a2) is located at said Focal Plane, (see (a—a) in FIG. 2d). To understand the present invention system, reference is again made to the well known Lens Equation:

$$(1/O)+(1/I)=(1/F);$$

or alternatively:

$$I=((F*O)/(O-F));$$

where "O" is the Object Distance, "I" the Image distance and "F" is the Focal Length (F) of the Secondary Focusing Optic (FL), which Focal Length (F) is chromatically corrected to a wavelength of electro-magnetic radiation utilized, (eg. two-hundred-fifty-four (254) nanometers where mercury is being analyzed). Now, in FIG. 1a, (which demonstrates prior art), the Object Distance "O", (of Secondary Focusing Optic (FL)), is assumed to be at infinity, (and is therefore not shown), because the Collimating Lens (CL) provides essentially parallel rays of radiation in Collimated Beam (CB). That being the case, the Lens Equation applicable to the prior art shown in FIG. 1a reduces to:

$$(1/I)=(1/F),$$

or alternatively stated:

$$(I)=(F).$$

That is to say, the Image Distance (I) of Secondary Focusing Optic (FL) becomes equal its Focal Distance "F". Thus, in the prior art system demonstrated in FIG. 1a, the Detector is typically placed in a focal plane located at a Focal Distance "F", of said Secondary Focusing Optic (FL), away from said Secondary Focusing Optic (FL). In said prior art focal plane, there typically appears an image of the Lamp bulb of Light Source (LS), which is the real "object" of the two element lens combination (FL) and (CL), (see FIG. 1a). In present invention demonstrated in FIGS. 2a–2d, however, the Object Distance "O" of Secondary Focusing Optic (FL) is no longer validly at Infinity, and the two element lens combination (FL) and (CL) focuses an image at a focal plane plane (a—a), (see FIG. 2d which provides an enlarged view of present invention optical imaging system elements at the right side in FIG. 2a). The present invention optical imaging system provides the object distance (and object location of said secondary focusing optic (FL)), be at the location of the Aperture (a1) of the Backlighted Primary Limiting Field Stop (PFS). This causes the Image Distance "I" of Secondary Focusing Optic (FL) to shift significantly to a point away from said Secondary Focusing Optic (FL) Focusing Length (F) by a distance (F') to a plane (F+F') from said Focal Length (FL), and the resultant image in plane (a—a) is a demagnified image of the Backlighted Primary Limiting Field Stop (PFS) aperture (a1). In the vicinity of that location, (F+F'), (see plane (a—a) in FIG. 2d), said Secondary Field Stop (SFS) is also physically present, which Secondary Field Stop (SFS) has an Aperture (a2) present therein. Said Aperture (a2) serves to isolate and pass therethrough a beam to Detector System (DET) in use, the intensity of which beam is representative of analyte presence and concentration in said essentially tubular shaped Long-Path Absorbance-Cell (LPAC), and does not pass internal reflection mediated aberrant rays, and changes therein based upon thermally induced movement effected etc. parameter changes in said essentially tubular shaped Long-Path Absorbance-Cell (LPAC), (eg. position, internal i.d. reflective wall cleanliness etc.), are blocked thereby. Said movements and cleanliness etc. effected changes are eliminated by removal of said aberrant "barrel-gleam" internal ray reflection component by Secondary Field Stop (SFS) Aperture (a2), as Aperature (a2) separates and blocks passage of said aberrant barrel-gleam component from said unreflected center-most beam which passes unhindered through said aperture (a2).

Figure 3:
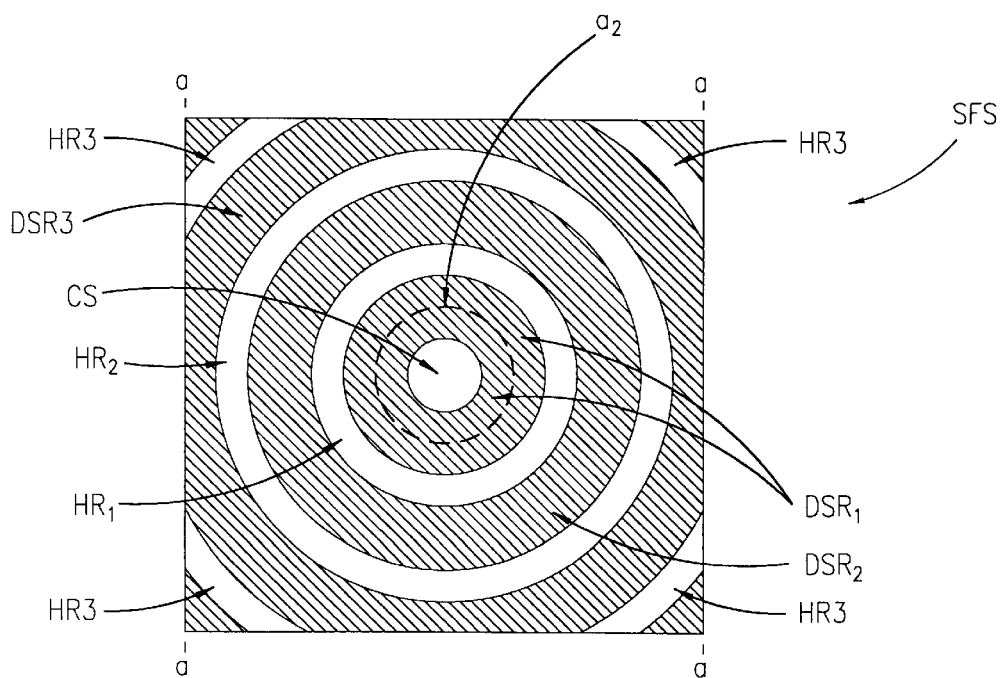
FIG. 3 shows a central spot (CS) image, three Light Halo-Ring images (HR1), (HR2) and (HR3), as well as three Dark Shadow-Ring images ((DSR1), (DSR2) and (DSR3), which present at plane (a—a) in FIG. 2d, at the location of secondary field stop aperture (a2).

To understand why this is the case, reference to FIG. 3 is instructive. FIG. 3 shows the Beam image appearance at plane (a—a) in FIG. 2d, (which is the present invention image plane of Focusing lens (FL) at distance (F+F') from (FL), (see FIG. 2a and 2c)), which image can be made to appear upon a fluorescent screen placed at said plane (a—a). (Note that optional filtering to provide rays representative of only desired wavelengths can be performed to facilitate and chromatically correct a human eye view of said image). Shown are a Central Spot (CS) image, and three Reflected demonstrative Concentric aberrant barrel-gleam "Light-Halo Rings", (HR1), (HR2) and (HR3), and three Dark Shadow-Rings (DSR1), (DSR2) and (DSR3). Said demonstrative "Light-Halo-Ring" images (HR1), (HR2) and (HR3) are produced by aberrant internal "Light-Pipe" reflection beam components, which reflections occur inside said essentially tubular shaped Long-Path Absorbance-Cell (LPAC), and said Central Spot is produced by a well collimated Beam component which, upon isolation from barrel-gleam, is not influenced by internal reflections, but rather passes straight through said essentially tubular shaped Long-Path Absorbance-Cell (LPAC), emphasis added. (Note, a plurality of aberrant "Light-Halo Rings" can actually be observed directly by looking into the distal end of a Long-Path Absorbance-Cell (LPAC) when an Aperture (a1) is placed at the first light source illuminated end of said essentially tubular shaped Long-Path Absorbance-Cell (LPAC)). It is to be understood that in present invention focal plane (a—a), and Detector (DET) positioned thereafter, said Central Spot (CS) intensity is not influenced by internal reflections which occur inside said essentially tubular shaped Long-Path Absorbance-Cell (LPAC), but that the intensity thereof is determined only by initial Collimated Beam (CB) intensity and absorption effected by analyte presence in said essentially tubular shaped Long-Path Absorbance-Cell (LPAC), again, emphasis added. Thus the orientation of said essentially tubular shaped Long-Path Absorbance-Cell (LPAC) can vary during use, (see the "Disclosure Of The Invention Section" of this Disclosure for typical representative relative numerical values associated with such variation), and the internal reflection causing surfaces of said essentially tubular shaped Long-Path Absorbance-Cell (LPAC) can become dirty etc. during use, causing variation in position and intensity of aberrant Light-Halo-Rings (HR1), (HR2) and (HR3) etc., while having no practical effect on the intensity of said Central Spot (CS). (That is, a margin of error of at least 0.006 inches at an image plane providing a demagnification ratio of 0.23 allow an object plane variation of ((0.006/0.23)=0.026), which allows movement immunity substantially exceeding all typically anticipated thermally induced motions in a present invention essentially tubular shaped Long-Path Absorbance-Cell (LPAC). Again, in focal plane (a—a), (see FIG. 2d), all reflection and barrel-gleam effects show up in, and are confined in, said Light-Halo-Rings (HR1), (HR2) and (HR3) etc., and not in the Central Spot (CS). Note further that in FIG. 3 that the Aperture (a2) is of a diameter large enough to pass the Central Spot (CS), (with a substantial margin of error for passage of essentially collimated rays), but not large enough to pass the Light-Halo Rings, (again with a substantial margin of error for blockage of the region of reflected rays). Thus the present invention is shown to provide a system which demonstrates greatly reduced sensitivity to reflection mediated changes in system element parameters, (eg. Long-Path Absorbance-Cell (LPAC) orientation changes and cleanliness affected changing internal reflective surface reflective properties etc.)

It is disclosed that the Light-Halo-Rings generally have diameters and band thicknesses which vary inversely with the inside diameter of the Aperture (a1) of said Backlighted Primary Limiting Field Stop (PFS) and directly with the inside diameter (D1) of said essentially tubular shaped Long-Path Absorbance-Cell (LPAC), hence, by proper user adjustment of said identified diameters, and that of said Secondary Field Stop (SFS) in a Long-Path Absorbance-Cell (LPAC) Absorption Photometry System, one can provide a present invention system which allows said Aperture (a2) in said Secondary Field Stop (SFS) to pass only said Central Spot (CS), and further to provide substantial error margin (ie. "safety-margin") for placement of aperture (a2) within inner-most "Dark Shadow-Ring" (DS1) surrounding Center Spot (CS). It is also disclosed that said pattern of Center Spot and Light Light-Halo-Rings distinctly separated by intervening Dark Shadow-Rings occurs only on the present invention focal plane (a—a), (as demonstrated in FIG. 3), which is located at distance (F+F') from said secondary focusing lens, (see FIGS. 2a and 2c), where said Center Spot is an image solely of said Backlighted Primary Limiting Field Stop (PFS), and does not appear in any other focal plane characterizing any other objects. For example, said image pattern of spacially resolved Center Spot and Light Light-Halo-Rings, separated by Dark Shadow-Rings does not occur in prior art focal plane (F) of FIGS. 1a and 1b characterizing prior art lamp image with both collimated and aberrant reflected rays superimposing and smearing over one another and not being separable to any appreciable degree, regardless of any aperture placement. Only with the present invention focal plane displaced to plane (a—a) at (F+F') and associated nearby planes, within "narrow" image plane depth-of-focus of Secondary Focusing Optic (FL), does an image present at the Secondary Field Stop (SFS) Aperture (a2) characterize the Backlighted Primary Limiting Field Stop (PFS) Aperture (a1) as object, (instead of the lamp), and only with present invention element placement, interrelational element dimensions, and use of said aperture (a1), does the FIG. 3 pattern of spacially resolved Central Spot Image and aberrant ray reflection effected Light Halo-Rings appear interposed between, and separated by, concentric Dark Shadow-Rings become manifest and visible to the eye on a fluorescent screen, or on a translucent fluorescent screen placed at plane (a—a). Again, it is to be appreciated that this allows the Center Spot (CS) to be isolatable by the secondary field stop (SFS), and free of the effects of reflections of aberrant rays in an imperfectly collimated beam CB) caused to pass through said Backlighted Primary Limiting Field Stop (PFS) Aperture (a1).

Note, that in the forgoing it is to be understood where a specific sample is being analyzed, the Focal Length (F+F') is preferably adjusted to effect a chromatic correction, and Wavelength Selection Means (FIL) are typically utilized to eliminate all but the wavelength(s) at which said specific sample is absorbant thereof. As well, a screen for viewing a FIG. 3 pattern of Light Light Halo-Rings and Dark Shadow-Rings will be typically be selected to provide strong fluorescence at said absorbed wavelength. (Note, it must be understood that said screen is not employed in actual operation of the present invention to obtain chemical analysis response to mercury or other analyte and is described only for purposes of describing how a visual demonstration can be performed).

It is to be noted that FIGS. 2b and 2c show expanded scale details of the Backlighted Primary Limiting Field Stop (PFS) region and Secondary Field Stop (SFS) region, respectively, which regions are shown in the context of an exemplary present invention optical imaging system, in FIG. 2a.

As optical proof, (testing), that the FIG. 3 Center Spot (CS) image comprises only unreflected (directly transmitted through an (LPAC) without reflections), rays and that the aberrant reflected rays are essentially confined to a larger diameter Light Halo-Ring, (eg. (HR1), (HR2) and (HR3) etc. in FIG. 3), separated from one another by Dark Shadow-Rings, (eg. DSR1), (DSR2) and (DSR3) etc. of FIG. 3), the following test results and conclusions are offered:

OPTICAL TEST: Loosen (LPAC) in its holder and selectively wiggle the (LPAC) as the only wiggled component while visually observing the resulting FIG. 3 demonstrated pattern on a temporarily utilized fluorescent translucent screen placed at (a—a), (see FIG. 2d). This wigling, of course, changes the angle at which aberrant rays approach and reflect from an inner surface of said (LPAC).

OPTICAL TEST RESULT: The Light Halo-Ring (HR1), (HR2) and (HR3) images wiggle in their entirety, while the Center Spot (CS) remains stationary, exhibiting no motion at all.

OPTICAL TEST CONCLUSION: (HR1), (HR2) and (HR3) comprise rays reflected from the wiggled (LPAC) inner wall, and Center Spot (CS) effecting rays do not interact with, touch or reflect from said (LPAC) inner walls.

Figure 4:
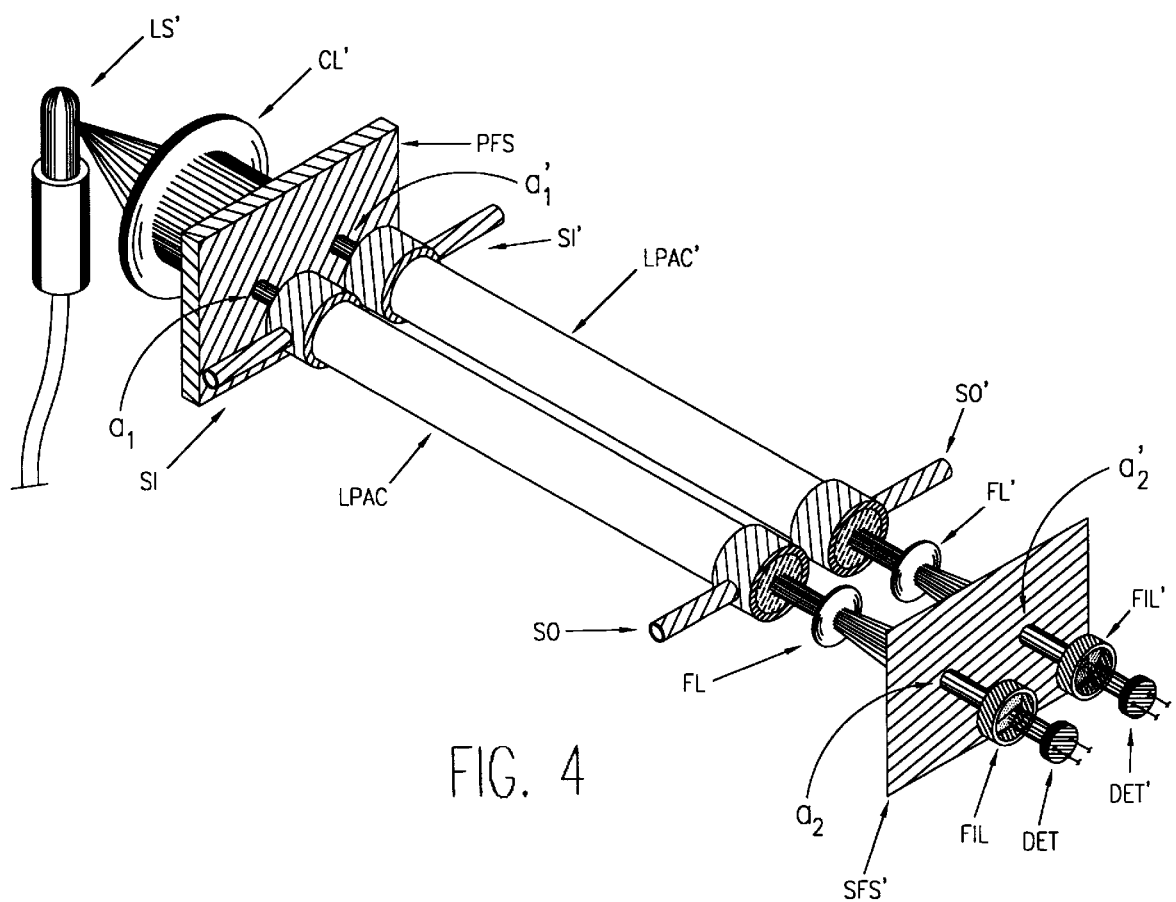
FIG. 4 shows a two component (double-beam) (LPAC) & (LPAC') present invention long-path absorbance-cell system, in which two long-path absorbance-cell components are present and separate in space.
Figure 5A:
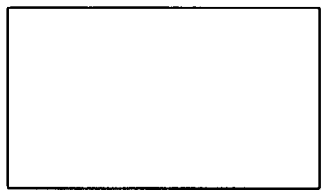
FIGS. 5a, 5b, 5c and 5d demonstrate alternative shapes for an internal bore of a present invention essentially tubular shaped long-path absorbance-cell system (LPAC).
Figure 5B:
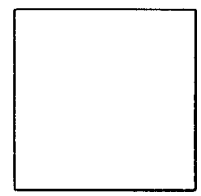
Figure 5C:
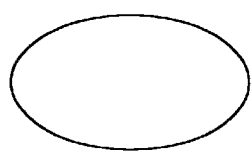
Figure 5D:
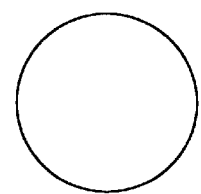

FIG. 4 shows a two component (LPAC) & (LPAC') Long-Path Absorbance-Cell (LPAC) system in which sample an reference (blank) intensities can be simultaneously monitored. Note that said two component Long-Path Absorbance-Cell (LPAC) system typically referred to as a "double-beam" system, typically has single element Light Source (LS), combined element Backlighted Primary Limiting Field Stop (PFS), combined element Secondary Field Stop (SFS) and combined element Detector System, (DET and DET'). Each Long-Path Absorbance-Cell (LPAC) and (LPAC'), with associated individual Backlighted Primary Limiting Field Stop (PFS) and Secondary Filed Stop (SFS) and Detector (DET) and (DET'), however, individually operates as described above.

Exemplary methods of use of single, and double beam present invention Long-Path Absorbance-Cell Imaging Systems were provided in the Disclosure of the Invention Section of this Disclosure.

Figure 6A:
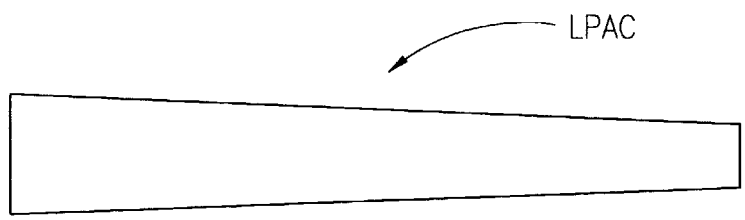
FIGS. 6a and 6b demonstrate non-constant internal diameters of an internal bore of a present invention essentially tubular shaped long-path absorbance-cell system (LPAC).
Figure 6B:
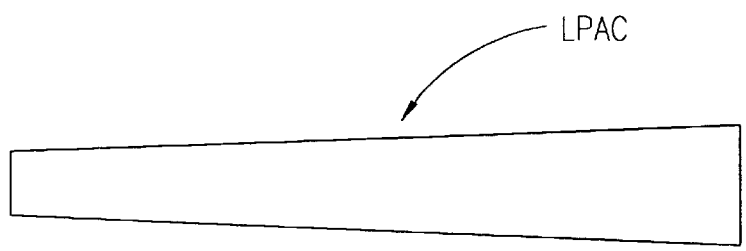

In this Disclosure the terminology "essentially tubular" has been used. Said terminology is to be understood to include circular, oval, rectangular, square and other functional cross sectional shapes. Of course, the term "diameter" is to be interpreted to denote a variable with respect to an angle of rotation about a central axis of a Long-Path Absorbance-Cell in cases, at a point along a length of an (LPAC), where other than a circular cross-section shape is present. In addition, the terminology "essentially tubular" should be interpreted as not requiring an outer dimension of an essentially tubular element to be of the same general cross-section as an inner dimension. For instance, an essentially circular cross-section inner diameter bore in a Long-Path Absorbance-Cell (LPAC) (LPAC') need not be accompanied by an essentially circular outer dimension cross-section. The only absolute requirement for a Long-Path Absorbance-Cell (LPAC) (LPAC') to considered as demonstrating an "essentially tubular" shape being that it have a continuous bore therethrough, through which a light beam can pass in use. (Note, the presence of UV Transparent Windows (UVWA) and (UVWB) at the ends of a Long-Path Absorbance-Cell (LPAC) (LPAC') are not to be considered as defeating of this general requirement. The continuous nature can be viewed with respect to UV radiation which effectively encounters a continuous bore). FIGS. 5a, 5b, 5c and 5d demonstrate non-limiting, non-circular, bore shapes, and FIGS. 6a and 6b demonstrate non-limiting, non-constant, bore diameters as a present invention essentially tubular Long-Path Absorbance-Cell is traversed from one side thereof to another.

It is also noted that the terminology "light" has been utilized to refer to electromagnetic radiation of any wavelength, and that a particularly important wavelength is two-hundred-fifty-four (254 nm) nanometers, where mercury detection is performed.

It should be understood as well, that the the element (FIL) can be any Wavelength Selection means, such as a filter, grating, spectrometer, acusto-optic-tunable-filter, interferometer, prism, prism spectrometer, etalon, a wavelength specific or descriminating detector (eg. RGB), or functional equivalents. As well, said element (FIL) can be positioned in any functional location in a present invention essentially tubular shaped Long-Path Absorbance-Cell (LPAC) system, with functional location meaning that the essentially Collimated Beam (CB) of light is caused to pass therethrough in use.

As well, the term "Lens", as used, should be interpreted sufficiently broadly to include optical focusing functional equivalents, such as properly employed mirrors and the like. As well, it is to be understood that a preferred Secondary Focusing Optic (FL) is a Lens, but can also be a mirror or mirror system.

In addition, the term "Collimated" should be interpreted to refer to a beam containing rays which are sufficiently parallel to function as truely collimated rays, (ie. avoiding wall reflections), even if not technically truely collimated, such as "long-focused" rays.

Finally essentially tubular shaped Long-Path Absorbance-Cell (LPAC) "parameters" which can change during use include element parameters per se., such as internal wall reflectivity, as well as positioning of system elements, such as (LPAC) movement.

Having hereby disclosed the subject matter of the present invention, it should be apparent that many modifications, substitutions, and variations of the present invention are possible in light thereof. It is therefore to be understood that the invention may be practiced other than as specifically described, and should be limited in breadth only by the Claims.

I claim:

1. An optical imaging system for use in long-path absorbance-cell absorbance photometry, which optical imaging system demonstrates decreased sensitivity to internal wall reflection mediated system element parameter change in use, which optical imaging system consists of at least one optical imaging system component, each of which at least one optical imaging system component(s) sequentially comprises as elements:

a light source;

a backlighted primary limiting field stop;

an essentially tubular shaped long-path absorbance-cell;

a secondary focusing optic;

a secondary field stop; and a light intensity detector system;

said backlighted primary limiting field stop and secondary field stop each comprising an aperture; said backlighted primary limiting field stop being placed at a distance essentially equivalent to the object distance of said secondary focusing optic away from said secondary focusing optic to one side of said secondary focusing optic, and said secondary field stop being placed in the vicinity of focal plane of said secondary focusing optic on an opposite side of said secondary focusing optic, such that said aperture in said secondary field stop is placed where a focused image of said backlighted primary limiting field stop aperture appears in use, when an essentially collimated beam of light originating from said light source is caused to pass through said aperture of said backlighted primary limiting field stop and said essentially tubular shaped long-path absorbance-cell; which focused image of said backlighted primary limiting field stop aperture demonstrates decreased sensitivity to internal wall reflection mediated system element parameter change because essentially only essentially collimated beam components which do not undergo reflection from internal walls of said essentially tubular shaped long-path absorbance-cell appear therein.

2. An optical imaging system for use in long-path absorbance-cell absorbance photometry as in claim 1 which further comprises at least one element selected from group consisting of a collimator optic and a wavelength selection means, said collimator optic, when present, being positioned with respect to said light source and backlighted primary limiting field stop so as to provide collimated light, derived from light provided by said light source, to said backlighted primary limiting field stop in use, and said wavelength selection means, when present, being positioned between said light source and said detector.

3. An optical imaging system for use in long-path absorbance-cell absorbance photometry as in claim 2 in which said collimated light is derived from said light source by a collimator optic means selected from the group consisting of: (a lens positioned between said light source and said backlighted primary limiting field stop with said light source being located essentially at the focal point of said lens, and a concave mirror with said light source placed at its focal point), such that collimated light produced is directed toward said backlighted primary limiting field stop.

4. An optical imaging system for use in long-path absorbance-cell absorbance photometry as in claim 2 in which said wavelength selection means is selected from the group consisting of: (a filter, a grating, a spectrometer, an intererometer, an acusto-optic tunable filter, an etalon, a prism, a prism spectrometer, and a wavelength specific detector, and combinations thereof).

5. An optical imaging system for use in long-path absorbance-cell absorbance photometry as in claim 1 in which the inner essentially tubular diameter of each present essentially tubular shaped long-path absorbance-cell is selected from the group consisting of: (essentially constant over the length thereof between first light source illuminated end of said essentially tubular shaped long-path absorbance-cell and said end of said essentially tubular shaped long-path absorbance-cell distal to said first light source illuminated end thereof, and not constant over said length).

6. An optical imaging system for use in long-path absorbance-cell absorbance photometry as in claim 1 in which the inner essentially tubular diameter of each present essentially tubular shaped long-path absorbance-cell is such as to provide a shape selected from the group consisting of circular, oval, elliptical, square and rectangular.

7. An optical imaging system for use in long-path absorbance-cell absorbance photometry as in claim 1 in which an inner surface of said essentially tubular shaped long-path absorbance-cell is caused to be nonreflective.

8. An optical imaging system for use in long-path absorbance-cell absorbance photometry as in claim 1 in which the number of optical imaging system components is two and the resulting system is a double beam absorbance photometer system.

9. An optical imaging system for use in long-path absorbance-cell absorbance photometry, which optical imaging system demonstrates decreased sensitivity to internal wall reflection mediated system element parameter change in use, which optical imaging system consists of at least one optical imaging system component, each of which at least one optical imaging system component sequentially comprises as elements:

a light source;
a backlighted primary limiting field stop;
an essentially tubular shaped long-path absorbance-cell;
a secondary focusing optic;
a secondary field stop; and
a light intensity detector system;

which backlighted primary limiting field stop and secondary field stop each comprise an aperture, and which essentially tubular shaped long-path absorbance-cell comprises an inner essentially tubular diameter, essentially transparent end windows, and means by which to cause an analyte containing sample to enter and pass therethrough in use; said backlighted primary limiting field stop aperture diameter being smaller than the inner essentially tubular diameter of said essentially tubular shaped long-path absorbance-cell and being positioned such that said backlighted primary limiting field stop aperture is essentially centrally located with respect to a relatively larger inner essentially tubular diameter first light source illuminated end of said essentially tubular shaped long-path absorbance-cell; which backlighted primary limiting field stop, in use, causes a light source initiated small diameter beam formed by passage through said backlighted primary limiting field stop aperture, to, as an essentially centrally located essentially collimated beam, via said essentially transparent end windows, enter, proceed through, and then exit said essentially tubular shaped long-path absorbance-cell at an end thereof distal to said first light source illuminated end thereof in the form of an essentially collimated central beam component which is essentially unaffected by reflection(s) of aberrant components of said small diameter essentially collimated beam from an inner wall within said essentially tubular shaped long-path absorbance-cell; and which backlighted primary limiting field stop aperture simultaneously casts a plurality of reflected concentric dark shadow-rings of progressively increasing diameter interior to said essentially tubular shaped long-path absorbance cell onto the inner wall of said essentially tubular shaped long path absorbance cell, which dark shadow-rings surround said essentially collimated central beam component, said dark shadow-rings being viewable through said end of said essentially tubular shaped long-path absorbance-cell distal to said first light source illuminated end thereof, an image of said backlighted primary limiting field stop aperture comprising essentially collimated central beam component being concentrically surrounded by said dark shadow-rings, each of which dark shadow-rings presents with substantial ring band thickness and has defined edge boundaries, said dark shadow-ring thicknesses varying inversely with the inside diameter of said backlighted primary limiting field stop aperture and directly with the inner diameter of said essentially tubular shaped long-path absorbance cell, said dark shadow-rings being separated from one another by interspersing light halo-ring reflections, the diameter of an essentially collimated beam at the location of said secondary field stop aperture being less than that of all but an innermost of said dark shadow-rings and less than all of said light halo-rings; said secondary focusing optic being situated past said distal end of said essentially tubular shaped long-path absorbance-cell and prior to said secondary field stop, with the location of said secondary field stop being situated in the vicinity of the image plane of said secondary focusing optic where the location of said backlighted primary limiting field stop aperture is taken as the secondary focusing optic object distance in the optic formula:

$$(1/O)+(1/I)=(1/F),$$

where "O" is the object distance from said secondary focusing optic to said backlighted primary limiting field stop aperture; "I" the image distance from said secondary focusing optic to said secondary field stop, and "F" is the focal length of said secondary focusing optic, the relative magnitudes of "O", "F" and "I" typically being selected to render object depth of focus of said secondary focusing optic sufficiently large to encompass said backlighted primary limiting field stop, all dark shadow-rings and all interspersed reflected light halo-rings; said secondary field stop aperture being concentrically positioned to allow passage of secondary focusing optic focused essentially centrally located image effecting small diameter essentially collimated beam therethrough, and entry thereof into said light intensity detector system, but said diameter of said secondary field stop aperture being smaller than of any of secondary focusing optic focused aberrant beam component reflection effected concentric light halo-rings, such that none of said light halo-rings are so passed by said secondary field stop aperture;

the result being that said essentially tubular shaped long-path absorbance-cell element parameters can change during use, resulting in changes in said plurality of reflected concentric dark shadow-rings of progressively increasing diameter and interspersing light halo-rings, without affecting the essentially centrally located image effecting backlighted primary limiting field stop essentially collimated beam effected reading of said light intensity detector system.

10. An optical imaging system for use in long-path absorbance-cell absorbance photometry as in claim 9 which further comprises at least one element selected from group consisting of a collimator optic and a wavelength selection means, said collimator optic, when present, being positioned with respect to said light source and backlighted primary limiting field stop so as to provide collimated light, derived from light provided by said light source, to said backlighted primary limiting field stop in use, and said wavelength selection means, when present, being positioned between said light source and said detector.

11. An optical imaging system for use in long-path absorbance-cell absorbance photometry as in claim 10 in which said collimated light is derived from said light source by a collimator optic means selected from the group consisting of: (a lens positioned between said light source and said backlighted primary limiting field stop with said light source being located essentially at the focal point of said lens, and a concave mirror with said light source placed at its focal point), such that collimated light produced is directed toward said backlighted primary limiting field stop.

12. An optical imaging system for use in long-path absorbance-cell absorbance photometry as in claim 10 in which said wavelength selection means is selected from the group consisting of: (a filter, a grating, a spectrometer, an intererometer, an acusto-optic tunable filter, an etalon, a prism, a prism spectrometer, and a wavelength specific detector, and combinations thereof).

13. An optical imaging system for use in long-path absorbance-cell absorbance photometry as in claim 9 in which the inner essentially tubular diameter of each present essentially tubular shaped long-path absorbance-cell is selected from the group consisting of: (essentially constant over the length thereof between first light source illuminated end of said essentially tubular shaped long-path absorbance-cell and said end of said essentially tubular shaped long-path absorbance-cell distal to said first light source illuminated end thereof, and not constant over said length).

14. An optical imaging system for use in long-path absorbance-cell absorbance photometry as in claim 9 in which the inner essentially tubular diameter of each present essentially tubular shaped long-path absorbance-cell is such as to provide a shape selected from the group consisting of circular, oval, elliptical, square and rectangular.

15. An optical imaging system for use in long-path absorbance-cell absorbance photometry as in claim 9 in which an inner surface of said essentially tubular shaped long-path absorbance-cell is caused to be nonreflective.

16. An optical imaging system for use in long-path absorbance-cell absorbance photometry as in claim 9 in which the number of optical imaging system components is two and the resulting system is a double beam absorbance photometer system.

17. A method of practicing long-path absorbance-cell photometry comprising the steps of:

a. providing an optical imaging system for use in long-path absorbance-cell absorbance photometry, which optical imaging system demonstrates decreased sensitivity to internal wall reflection mediated system element parameter change in use, which optical imaging system consists of at least one optical imaging system component, each of which at least one optical imaging system component(s) sequentially comprises as elements:

a light source;
a backlighted primary limiting field stop;
an essentially tubular shaped long-path absorbance-cell;
a secondary focusing optic;
a secondary field stop; and
a light intensity detector system;

said backlighted primary limiting field stop and secondary field stop each comprising an aperture; said backlighted primary limiting field stop being placed at a distance essentially equivalent to the object distance of said secondary focusing optic away form said secondary focusing optic to one side of said secondary focusing optic, and said secondary field stop being placed in the vicinity of focal plane of said secondary focusing optic on an opposite side of said secondary focusing optic, such that said aperture in said secondary field stop is placed where a focused image of said backlighted primary limiting field stop aperture appears in use, when an essentially collimated beam of light originating from said light source is caused to pass through said aperture of said backlighted primary limiting field stop and said essentially tubular shaped long-path absorbance-cell; which focused image of said backlighted primary limiting field stop aperture demonstrates decreased sensitivity to internal wall reflection mediated system element parameter change because essentially only essentially collimated beam components which do not undergo reflection from internal walls of said essentially tubular shaped long-path absorbance-cell appear therein;

said method further comprising, in a functional order, the steps of:

b. causing a blank without analyte content to pass through an essentially tubular shaped long-path absorbance-cell;

c. simultaneous with step b., causing a beam of light from a light source to pass through and exit a backlighted primary field stop aperture associated with a essentially tubular shaped long-path absorbance-cell, said essentially tubular shaped long-path absorbance-cell, and an aperture of an associated secondary field stop, then enter a detector system wherein the intensity, at desired wavelength(s), thereof is determined;

d. optionally causing a light absorbing analyte containing known concentration standard sample to pass through the same essentially tubular shaped long-path absorbance-cell;

e. optionally, but simultaneous with optional step d. if performed, causing a beam of light from a light source to pass through and exit said backlighted primary field stop aperture, said essentially tubular shaped long-path absorbance-cell, and said aperture of said secondary field stop, then enter said detector system wherein the intensity, at desired wavelength(s), thereof is determined;

f. causing a light absorbing analyte containing unknown concentration sample to pass through the same essentially tubular shaped long-path absorbance-cell;

g. simultaneous with step e., causing a beam of light from said light source to pass through and exit said primary field stop aperture, said essentially tubular shaped long-path absorbance-cell, and said aperture of said secondary field stop, then enter said detector system wherein the intensity, at desired wavelength(s), thereof is determined;

h. comparing the light intensity results determined in steps c., e. and g., and computing absorbance values therefrom using photometry laws; and i. from the computed absorbance values in step h., and the known concentration standard sample analyte content, determining the analyte content of said unknown analyte containing sample caused to pass through said essentially tubular shaped long-path absorbance-cell in step f.

18. A method of practicing long-path absorbance-cell photometry as in claim 17 in which the step of determining the analyte content of said unknown analyte containing sample involves mercury as the analyte.

19. A method of practicing long-path absorbance-cell photometry comprising the steps of:

a. providing an optical imaging system for use in long-path absorbance-cell absorbance photometry, which optical imaging system demonstrates decreased sensitivity to internal wall reflection mediated system element parameter change in use, which optical imaging system consists of at least one optical imaging system component, each of which at least one optical imaging system component(s) sequentially comprises as elements:
a light source;
a backlighted primary limiting field stop;
an essentially tubular shaped long-path absorbance-cell;
a secondary focusing optic;
a secondary field stop; and
a light intensity detector system;

said backlighted primary limiting field stop and secondary field stop each comprising an aperture; said backlighted primary limiting field stop being placed at a distance essentially equivalent to the object distance of said secondary focusing optic away from said secondary focusing optic to one side of said secondary focusing optic, and said secondary field stop being placed in the vicinity of focal plane of said secondary focusing optic on an opposite side of said secondary focusing optic, such that said aperture in said secondary field stop is placed where a focused image of said backlighted primary limiting field stop aperture appears in use, when an essentially collimated beam of light originating from said light source is caused to pass through said aperture of said backlighted primary limiting field stop and said essentially tubular shaped long-path absorbance-cell; which focused image of said backlighted primary limiting field stop aperture demonstrates decreased sensitivity to internal wall reflection mediated system element parameter change because essentially only essentially collimated beam components which do not undergo reflection from internal walls of said essentially tubular shaped long-path absorbance-cell appear therein;

said method further comprising, in a functional order, the steps of:

b. causing a light absorbing analyte containing unknown concentration sample, and optionally, sequentially, a light absorbing analyte containing known concentration sample to pass through a first essentially tubular shaped long-path absorbance-cell;

c. simultaneous with step b., causing a beam of light from a light source to pass through and exit a backlighted primary field stop aperture associated with a first essentially tubular shaped long-path absorbance-cell, said essentially tubular shaped long-path absorbance-cell, and an aperture of an associated secondary field stop, then enter a detector system wherein the intensity, at desired wavelength(s) for the present sample(s) is determined;

d. simultaneous with step b. causing a blank without analyte content present therein to pass through a second essentially tubular shaped long-path absorbance-cell;

e. simultaneous with step d., causing a beam of light from said light source to pass through and exit a backlighted primary field stop aperture associated with said second essentially tubular shaped long-path absorbance-cell, said second essentially tubular shaped long-path absorbance-cell, and an aperture of an associated secondary field stop, then enter a detector system wherein the intensity, at desired wavelength(s), thereof is determined;

f. comparing the light intensity results determined in steps c. and e., and computing absorbance values therefrom using photometry laws; and g. from the computed absorbance values in step f., and a known concentration standard sample analyte content, determining the analyte content of said unknown analyte containing sample caused to pass through said essentially tubular shaped long-path absorbance-cell in step b.

20. A method of practicing long-path absorbance-cell photometry as in claim 19 in which the step of determining the analyte content of said unknown analyte containing sample involves mercury as the analyte.

21. A method of practicing long-path absorbance-cell photometry comprising the steps of:

a. providing an optical imaging system for use in long-path absorbance-cell absorbance photometry, which optical imaging system demonstrates decreased sensitivity to internal wall reflection mediated system element parameter change in use, which optical imaging system consists of at least one optical imaging system component, each of which at least one optical imaging system component sequentially comprises as elements:
a light source;
a backlighted primary limiting field stop;
an essentially tubular shaped long-path absorbance-cell;
a secondary focusing optic;
a secondary field stop; and
a light intensity detector system;

which backlighted primary limiting field stop and secondary field stop each comprise an aperture, and which essentially tubular shaped long-path absorbance-cell comprises an inner essentially tubular diameter, essentially transparent end windows, and means by which to cause an analyte containing sample to enter and pass therethrough in use; said backlighted primary limiting field stop aperture diameter being smaller than the inner essentially tubular diameter of said essentially tubular shaped long-path absorbance-cell and being positioned such that said backlighted primary limiting field stop aperture is essentially centrally located with respect to a relatively larger inner essentially tubular diameter first light source illuminated end of said essentially tubular shaped long-path absorbance-cell; which backlighted primary limiting field stop, in use, causes a light source initiated small diameter beam formed by passage through said backlighted primary limiting field stop aperture, to, as an essentially centrally located essentially collimated beam, via said essentially transparent end windows, enter, proceed through, and then exit said essentially tubular shaped long-path absorbance-cell at an end thereof distal to said first light source illuminated end thereof in the form of an essentially collimated central beam component which is essentially unaffected by reflection(s) of aberrant components of said small diameter essentially collimated beam from an inner wall within said essentially tubular shaped long-path absorbance-cell; and which backlighted primary limiting field stop aperture simultaneously casts a plurality of reflected concentric dark shadow-rings of progressively increasing diameter interior to said essentially tubular shaped long-path absorbance cell onto the inner wall of said essentially tubular shaped long path absorbance cell, which dark shadow-rings surround said essentially collimated central beam component, said dark shadow-rings being viewable through said end of said essentially tubular shaped long-path absorbance-cell distal to said first light source illuminated end thereof, an image of said backlighted primary limiting field stop aperture comprising essentially collimated central beam component being concentrically surrounded by said dark shadow-rings, each of which dark shadow-rings presents with substantial ring band thickness and has defined edge boundaries, said dark shadow-ring thicknesses varying inversely with the inside diameter of said backlighted primary limiting field stop aperture and directly with the inner diameter of said essentially tubular shaped long-path absorbance cell, said dark shadow-rings being separated from one another by interspersing light halo-ring reflections, the diameter of an essentially collimated beam at the location of said secondary field stop aperture being less than that of all but an innermost of said dark shadow-rings and less than all of said light halo-rings; said secondary focusing optic being situated past said distal end of said essentially tubular shaped long-path absorbance-cell and prior to said secondary field stop, with the location of said secondary field stop being situated in the vicinity of the image plane of said secondary focusing optic where the location of said backlighted primary limiting field stop aperture is taken as the secondary focusing optic object distance in the optic formula:

$(1/O)+(1/I)=(1/F)$, where "O" is the object distance from said secondary focusing optic to said backlighted primary limiting field stop aperture; "I" the image distance from said secondary focusing optic to said secondary field stop, and "F" is the focal length of said secondary focusing optic, the relative magnitudes of "O", "F" and "I" typically being selected to render object depth of focus of said secondary focusing optic sufficiently large to encompass said backlighted primary limiting field stop, all dark shadow-rings and all interspersed reflected light halo-rings; said secondary field stop aperture being concentrically positioned to allow passage of secondary focusing optic focused essentially centrally located image effecting small diameter essentially collimated beam therethrough, and entry thereof into said light intensity detector system, but said diameter of said secondary field stop aperture being smaller than of any of secondary focusing optic focused aberrant beam component reflection effected concentric light halo-rings, such that none of said light halo-rings are so passed by said secondary field stop aperture;

the result being that said essentially tubular shaped long-path absorbance-cell element parameters can change during use, resulting in changes in said plurality of reflected concentric dark shadow-rings of progressively increasing diameter and interspersing light halo-rings, without affecting the essentially centrally located image effecting backlighted primary limiting field stop essentially collimate beam effected reading of said light intensity detector system;

said method further comprising, in a functional order, the steps of:

b. causing a blank without analyte content to pass through an essentially tubular shaped long-path absorbance-cell;

c. simultaneous with step b., causing a beam of light from a light source to pass through and exit a backlighted primary field stop aperture associated with a essentially tubular shaped long-path absorbance-cell, said essentially tubular shaped long-path absorbance-cell, and an aperture of an associated secondary field stop, then enter a detector system wherein the intensity, at desired wavelength(s), thereof is determined;

d. optionally causing a light absorbing analyte containing known concentration standard sample to pass through the same essentially tubular shaped long-path absorbance-cell;

e. optionally, but simultaneous with optional step d. if performed, causing a beam of light from a light source to pass through and exit said backlighted primary field stop aperture, said essentially tubular shaped long-path absorbance-cell, and said aperture of said secondary field stop, then enter said detector system wherein the intensity, at desired wavelength(s), thereof is determined;

f. causing a light absorbing analyte containing unknown concentration sample to pass through the same essentially tubular shaped long-path absorbance-cell;

g. simultaneous with step e., causing a beam of light from said light source to pass through and exit said primary field stop aperture, said essentially tubular shaped long-path absorbance-cell, and said aperture of said secondary field stop, then enter said detector system wherein the intensity, at desired wavelength(s), thereof is determined;

h. comparing the light intensity results determined in steps c., e. and g., and computing absorbance values therefrom using photometry laws; and i. from the computed absorbance values in step h., and the known concentration standard sample analyte content, determining the analyte content of said unknown analyte containing sample caused to pass through said essentially tubular shaped long-path absorbance-cell in step f.

22. A method of practicing long-path absorbance-cell photometry as in claim 21 in which the step of determining the analyte content of said unknown analyte containing sample involves mercury as the analyte.

23. A method of practicing long-path absorbance-cell photometry comprising the steps of:

a. providing an optical imaging system for use in long-path absorbance-cell absorbance photometry, which optical imaging system demonstrates decreased sensitivity to internal wall reflection mediated system element parameter change in use, which optical imaging system consists of at least one optical imaging system component, each of which at least one optical imaging system component sequentially comprises as elements:
  a light source;
  a backlighted primary limiting field stop;
  an essentially tubular shaped long-path absorbance-cell;
  a secondary focusing optic;
  a secondary field stop; and
  a light intensity detector system;
which backlighted primary limiting field stop and secondary field stop each comprise an aperture, and which essentially tubular shaped long-path absorbance-cell comprises an inner essentially tubular diameter, essentially transparent end windows, and means by which to cause an analyte containing sample to enter and pass therethrough in use; said backlighted primary limiting field stop aperture diameter being smaller than the inner essentially tubular diameter of said essentially tubular shaped long-path absorbance-cell and being positioned such that said backlighted primary limiting field stop aperture is essentially centrally located with respect to a relatively larger inner essentially tubular diameter first light source illuminated end of said essentially tubular shaped long-path absorbance-cell; which backlighted primary limiting field stop, in use, causes a light source initiated small diameter beam formed by passage through said backlighted primary limiting field stop aperture, to, as an essentially centrally located essentially collimated beam, via said essentially transparent end windows, enter, proceed through, and then exit said essentially tubular shaped long-path absorbance-cell at an end thereof distal to said first light source illuminated end thereof in the form of an essentially collimated central beam component which is essentially unaffected by reflection(s) of aberrant components of said small diameter essentially collimated beam from an inner wall within said essentially tubular shaped long-path absorbance-cell; and which backlighted primary limiting field stop aperture simultaneously casts a plurality of reflected concentric dark shadow-rings of progressively increasing diameter interior to said essentially tubular shaped long-path absorbance cell onto the inner wall of said essentially tubular shaped long path absorbance cell, which dark shadow-rings surround said essentially collimated central beam component, said dark shadow-rings being viewable through said end of said essentially tubular shaped long-path absorbance-cell distal to said first light source illuminated end thereof, an image of said backlighted primary limiting field stop aperture comprising essentially collimated central beam component being concentrically surrounded by said dark shadow-rings, each of which dark shadow-rings presents with substantial ring band thickness and has defined edge boundaries, said dark shadow-ring thicknesses varying inversely with the inside diameter of said backlighted primary limiting field stop aperture and directly with the inner diameter of said essentially tubular shaped long-path absorbance cell, said dark shadow-rings being separated from one another by interspersing light halo-ring reflections, the diameter of an essentially collimated beam at the location of said secondary field stop aperture being less than that of all but an innermost of said dark shadow-rings and less than all of said light halo-rings; said secondary focusing optic being situated past said distal end of said essentially tubular shaped long-path absorbance-cell and prior to said secondary field stop, with the location of said secondary field stop being situated in the vicinity of the image plane of said secondary focusing optic where the location of said backlighted primary limiting field stop aperture is taken as the secondary focusing optic object distance in the optic formula:

$$(1/O)+(1/I)=(1/F),$$

where "O" is the object distance from said secondary focusing optic to said backlighted primary limiting field stop aperture; "I" the image distance from said secondary focusing optic to said secondary field stop, and "F" is the focal length of said secondary focusing optic, the relative magnitudes of "O", "F" and "I" typically being selected to render object depth of focus of said secondary focusing optic sufficiently large to encompass said backlighted primary limiting field stop, all dark shadow-rings and all interspersed reflected light halo-rings; said secondary field stop aperture being concentrically positioned to allow passage of secondary focusing optic focused essentially centrally located image effecting small diameter essentially collimated beam therethrough, and entry thereof into said light intensity detector system, but said diameter of said secondary field stop aperture being smaller than of any of secondary focusing optic focused aberrant beam component reflection effected concentric light halo-rings, such that none of said light halo-rings are so passed by said secondary field stop aperture;

the result being that said essentially tubular shaped long-path absorbance-cell element parameters can change during use, resulting in changes in said plurality of reflected concentric dark shadow-rings of progressively increasing diameter and interspersing light halo-rings, without affecting the essentially centrally located image effecting backlighted primary limiting field stop essentially collimated beam effected reading of said light intensity detector system;

said method further comprising, in a functional order, the steps of:

b. causing a light absorbing analyte containing unknown concentration sample, and optionally, sequentially, a light absorbing analyte containing known concentration sample to pass through a first essentially tubular shaped long-path absorbance-cell;

c. simultaneous with step b., causing a beam of light from a light source to pass through and exit a backlighted primary field stop aperture associated with a first essentially tubular shaped long-path absorbance-cell, said essentially tubular shaped long-path absorbance-cell, and an aperture of an associated secondary field stop, the enter a detector system wherein the intensity, at desired wavelength(s) for the present sample(s) is determined;

d. simultaneous with step b. causing a blank without analyte content present therein to pass through a second essentially tubular shaped long-path absorbance-cell;

e. simultaneous with step d., causing a beam of light from said light source to pass through and exit a backlighted primary field stop aperture associated with said second essentially tubular shaped long-path absorbance-cell, said second essentially tubular shaped long-path absorbance-cell, and an aperture of an associated secondary field stop, then enter a detector system wherein the intensity, at desired wavelength(s), thereof is determined;

f. comparing the light intensity results determined in steps c. and e., and computing absorbance values therefrom using photometry laws; and g. from the computed absorbance values in step f., and a known concentration standard sample analyte content, determining the analyte content of said unknown analyte containing sample caused to pass through said essentially tubular shaped long-path absorbance-cell in step b.

24. A method of practicing long-path absorbance-cell photometry as in claim 23 in which the step of determining the analyte content of said unknown analyte containing sample involves mercury as the analyte mercury as the analyte.

* * * * *